(12) United States Patent
Ikariya et al.

(10) Patent No.: US 6,887,820 B1
(45) Date of Patent: May 3, 2005

(54) METHOD FOR PRODUCING OPTICALLY ACTIVE COMPOUNDS

(75) Inventors: Takao Ikariya, Tokyo (JP); Shohei Hashiguchi, Osaka (JP); Jun Takehara, Ibaraki (JP); Nobuyuki Uematsu, Okayama (JP); Kazuhiko Matsumura, Aichi (JP); Ryoji Noyori, Aichi (JP); Akio Fujii, Kanagawa (JP)

(73) Assignees: Japan Science and Technology Corporation, Saitama (JP); NKK Corporation, Tokyo (JP); Takeda Pharmaceutical Company Limited, Osaka (JP); Asahi Kasei Pharma Corporation, Tokyo (JP); Takasago International Corporation, Tokyo (JP)

( * ) Notice: Subject to any disclaimer, the term of this patent is extended or adjusted under 35 U.S.C. 154(b) by 0 days.

(21) Appl. No.: 09/661,560

(22) Filed: Sep. 14, 2000

Related U.S. Application Data

(62) Division of application No. 09/077,787, filed as application No. PCT/JP96/03573 on Dec. 6, 1996, now Pat. No. 6,184,381.

(30) Foreign Application Priority Data

Dec. 6, 1995 (JP) .............................. 7-318303
Dec. 6, 1995 (JP) .............................. 7-318304
Oct. 25, 1996 (JP) .............................. 8-284233

(51) Int. Cl.$^7$ .......... B01J 31/00; C07F 15/00; C07C 37/00
(52) U.S. Cl. .......... 502/155; 556/22; 556/23; 556/137; 568/783
(58) Field of Search .......... 502/155; 556/22, 556/23, 137; 568/783

(56) References Cited

U.S. PATENT DOCUMENTS 6,486,337 B2 * 11/2002 Burk et al. .................. 556/22

FOREIGN PATENT DOCUMENTS

| JP | 07285983 | 10/1995 |
| JP | 08225466 | 9/1996 |
| JP | 08310981 | 11/1996 |

* cited by examiner

Primary Examiner—Porfirio Nazario-Gonzalez
(74) Attorney, Agent, or Firm—Wenderoth, Lind & Ponack, L.L.P.

(57) ABSTRACT

A method for producing optically active compounds is disclosed. The method is highly practical for producing optically active compounds useful for various utilities such as intermediates for synthesizing pharmaceutical agents, liquid crystal materials and agents for optical resolution.

9 Claims, No Drawings

METHOD FOR PRODUCING OPTICALLY ACTIVE COMPOUNDS

This Application is a Divisional Application of Ser. No 09/077,787, filed Sep. 29, 1998, now U.S. Pat. No. 6,184,381, which is a 371 of PCT/JP96/03523 filed Dec. 6, 1996.

BACKGROUND OF THE INVENTION

1. Field of the Invention

The present invention relates to a method for producing optically active compounds such as optically active alcohols and optically active amines. More specifically, the present invention relates to a novel, highly practical method for producing optically active compounds useful for various utilities such as intermediates for synthesizing pharmaceutical chemicals, liquid crystal materials and agents for optical resolution.

2. Description of the Related Art

Various methods for producing optically active compounds have been known conventionally. As the method for asymmetrically synthesis of optically active alcohol compounds, for example, the following methods have been known;

(1) a method by using enzymes such as baker's yeast; and
(2) a method for asymmetric hydrogenation of carbonyl compounds by using metal complex catalysts. For the method (2), in particular, a great number of examples of asymmetric catalytic reactions have been reported for example as follows;
(1) an asymmetric hydrogenation of carbonyl compounds with functional groups, by means of optically active ruthenium catalysts, as described in detail in Asymmetric Catalysis in organic Synthesis, Ed. R. Noyori., pp. 56–82 (1994); (2) a method through hydrogen transfer-type reduction by means of chiral complex catalysts of ruthenium, rhodium or iridium, as described in Chem. Rev., Vol. 92, pp. 1051–1069 (1992); (3) a process of asymmetric hydrogenation tartaric acid by means of a modified nickel catalyst with tartaric acid as described in Oil Chemistry, pp.882–831 (1980) and Advances in Catalysis, Vol.32, pp.215 (1983), Ed. Y. Izumi; (4) an asymmetric hydrosilylation method, as described in Asymmetric Synthesis, Vol.5, Chap.4 (1985), Ed. J. D. Morrison and J. Organomet. Chem. Vol.346, pp.413–424 (1988); and (5) a borane reduction process in the presence of chiral ligands as described J. Chem. Soc., Perkin Trans.1, pp.2039–2044 (1985) and J. Am. Chem. Soc., Vol.109, pp. 5551–5553 (1987).

By the conventional method by means of enzymes, however, alcohols can be recovered at a relatively high optical purity, but the reaction substrate therefor is limited and the absolute configuration in the resulting alcohols is limited to specific one. By the asymmetric hydrogen hydrogenation method by means of transition metal complex catalysts, optically active alcohols can be produced at a high selectivity, but a pressure-resistant reactor is required therefor because hydrogen gas is used as the hydrogen source, which is disadvantageous in terms of operational difficulty and safety. Furthermore, the method through such asymmetric hydrogen transfer-type reduction by using conventional metal complex catalysts is limited in that the method requires reaction conditions under heating and the reaction selectivity is insufficient, disadvantageously in practical sense.

Accordingly, it has been desired conventionally that a new, very general method for synthesizing optically active alcohols by using a highly active and highly selective catalyst with no use of hydrogen gas be achieved.

But no highly efficient and highly selective method for producing such secondary alcohols through asymmetric synthetic reaction by using catalysts similar to those described above has been established yet. As to the optically active secondary alcohols, a method for synthesizing optically active secondary alcohols via optional resolution of racemic secondary alcohols has been known for some reaction substrate which can hardly be reduced, although an excellent optical purity is hardly attained. (Asymmetric Catalysis in Organic Synthesis, Ed. R. Noyori). Because hydrogen transfer-type reduction is a reversible reaction according to the method, dehydrogenation-type oxidation as its adverse reaction is used according to the method. Therefore, the method is called as kinetic optical resolution method. According to the method, however, no process of producing optically active secondary alcohols with catalysts at a high efficiency has been reported yet.

As the method for synthetically producing optically active amine compounds, furthermore, a process of optically resolving once produced racemic compounds by using optically active acids and a process through asymmetric synthetic reaction have been known. By the optical resolution process, however, optically active acids should be used at an equal amount or more to amine compounds disadvantageously and complex procedures such as crystallization, separation and purification are required so as to recover optically active amine compounds. As the method through asymmetric synthesis, alternatively, the following processes have been known; (1) an enzymatic process; (2) a process by using metal hydride compounds; and (3) a process of asymmetric hydrogenation by using metal complex catalysts. As to the process by using metal hydride compounds as described above in (2), a great number of reports have been issued about a process of asymmetrically reducing carbon-nitrogen multiple bonds by using an metal hydrides with chiral modifiers. As a general process thereof, for example, it has been known a stoichiometric reduction process of imine compounds and oxime compounds by using a metal hydrides with an optically active ligand, as described in Comprehensive Organic Synthesis, EdS. B. M. Trost and I. Flemming, Vol.8, p.25 (1991), Organic Preparation and Procedures Inc. O. Zhu, R. O. Hutchins, and M. K. Huchins, Vol.26(2), pp.193–235 (1994) and Japanese Patent Laid-open No. 2-311446. The process includes a number of processes with excellent reaction selectivity, but these processes are disadvantageous because that these processes require the use of a reaction agent at an equivalent weight or more to a reaction substrate, along with neutralization treatment after the reaction and additionally in that these processes require laborious purification procedures to recover optically active substances. As the process of asymmetric hydrogenation of carbon-nitrogen multiple bonds by using metal complex catalysts as the method (3), it has been known an asymmetric hydrogenation process of imine compounds with functional groups, by means of optically active metal complex catalysts, as described in Asymmetric Catalysis inorganic Synthesis, pp.82–85 (1994), Ed. R. Noyori. But the process has a drawback in terms of reaction velocity and selectivity.

By the method by using enzymes as the method (1), furthermore, amines at a relatively high optical purity can be recovered, but the reaction substrates are limited and the resulting amines have only specific absolute configurations. Furthermore, at a process of asymmetric hydrogenation by means of complex catalysts of transition metals using hydrogen gas, optically active amines have not yet been recovered at a high selectivity or pressure-resistant reactors are essentially required because hydrogen gas is used as the hydrogen source. Hence, such process is disadvantageous because of technically difficult operation and safety problems.

Accordingly, it has been demanded that a novel method for synthesizing an optically active amine by using a very common, highly active and highly selective catalyst be realized.

Alternatively, a great number of transition metal complexes have been used conventionally as catalysts for organic metal reactions; particularly because rare metal complexes are highly active and stable with the resultant ready handleability despite of high cost, synthetic reactions using the complexes have been developed. The progress of such synthetic reactions using chiral complex catalysts is innovative, and a great number of reports have been issued, reporting that highly efficient organic synthetic reactions have been realized.

Among them, a great number of asymmetric reactions using chiral complexes catalysts with optically active phosphine ligands as the catalysts therefor have already been developed, and some of them have been applied industrially (Asymmetric Catalysis in Organic Synthesis, Ed. R. Noyori).

As complexes of optically active nitrogen compounds coordinated with transition metals such as ruthenium, rhodium and iridium, a great number of such complexes additionally having excellent properties as catalysts for asymmetric synthetic action have been known. So as to enhance the properties of these catalysts, a great number of propositions concerning the use of optically active nitrogen compounds of specific structures have been done (Chem. Rev., Vol.92, pp.1051–1069 (1992)).

For example, reports have been issued about (1) optically active 1,2-diphenylethylenediamines and rhodium-diamine complexes with ligands of cyclohexanediamines, as described in Tetrahedron Asymmetry, Vol.6, pp.705–718 (1995); (2) ruthenium-imide complex with ligands of optically active bisaryliminocyclohexanes, as described in Tetrahedron, Vol. 50, pp.4347–4354 (1994); (3) iridium-pyridine complex with ligands of pyridines, as described in Japanese Patent Laid-open Nos. 62-281861 and 63-119465; (4) optically active 1,2-diphenylethylenediamines or iridium-diamine complex with ligands of cyclohexanediamines, as described in Japanese Patent Laid-open No.62-273990; (5) ruthenium-diamine complex of RuCl[p-TsNCH($C_6H_5$)CH($C_6H_5$)$NH_2$] (arene) (chloro-(N-p-toluenesulfonyl-1,2-diphenylethylenediamine)(arene) ruthenium) (arene represents benzene which may or may not have a substituent), which is produced by coordinating ruthenium with optically active N-p-toluenesulfonyl-1,2-diphenylethylenediamine [referred to as "p-TsNHCH($C_6H_5$)CH($C_6H_5$)$NH_2$" hereinabove and below], as described in J. Am. Chem. Soc., Vol.117, pp.7562–7563(1995); J. Am. Chem. Soc., Vol.118, pp.2521–2522 (1996) and J. Am. Chem. Soc., Vol.118, pp.4916–4917 (1996).

Even if these complexes are used, however, problems currently remain to be overcome for practical use, including insufficient catalyst activities, sustainability and optical purities, depending on the subjective reactions and reaction substrates.

SUMMARY OF THE INVENTION

So as to overcome the aforementioned problems, the present invention is to provide a method for producing optically active compounds, comprising subjecting a compound represented by the following formula (I);

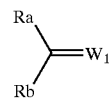

(wherein Ra and Rb independently represent a linear or cyclic hydrocarbon group or heterocyclic group which may or may not have a substituent; $W_1$ represents oxygen atom, N-H, N-Rc, N-OH or N-O-Rd; and Rc and Rd represent the same hydrocarbon group or heterocyclic group as described above) to transfer-type asymmetric reduction in the presence of a transition metal complex and an optically active nitrogen-containing compound or a transition metal complex with an optically active nitrogen-containing compound as an asymmetric ligand, along with a hydrogen-donating organic or inorganic compound, to produce an optically active compound represented by the following formula (II);

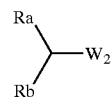

(wherein $W_2$ represents OH, NH2, NH-Rc, NH-OH or NH-O-Rd; and Ra, Rb, Rc and Rd independently represent the same as those described above).

Additionally, the present invention is to provide a method for producing an optically active alcohol according to the aforementioned method, comprising asymmetrically reducing a carbonyl compound represented by the following formula (III);

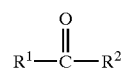

(wherein $R^1$ represents an aromatic hydrocarbon group, a saturated or unsaturated aliphatic hydrocarbon group or cyclic aliphatic hydrocarbon group, which may or may not have a substituent, or a heterocyclic group which may or may not have a substituent and contains hetero atoms such as nitrogen, oxygen, sulfur atoms and the like as atoms composing the ring; $R^2$ represents hydrogen atom, a saturated or unsaturated aliphatic hydrocarbon group or cyclic aliphatic hydrocarbon group which may or may not have a substituent, or an aromatic hydrocarbon group, or the same heterocyclic group as described above; and $R^1$ and $R^2$ may satisfactorily be bonded together to form a ring), to produce an optically active alcohol represented by the following formula (IV);

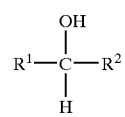

(wherein $R^1$ and $R^2$ are the same as described above).

Furthermore, the present invention is to provide a method for producing an optically active amine, comprising asymmetrically reducing an imine compound represented by the following formula (V);

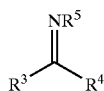

(wherein $R^3$ represents an aromatic hydrocarbon group, a saturated or unsaturated aliphatic hydrocarbon group or cyclic aliphatic hydrocarbon group, which may or may not have a substituent, or a heterocyclic group which may or may not have a substituent and contains hetero atoms such as nitrogen, oxygen, sulfur atoms and the like as atoms composing the ring; $R^4$ represents hydrogen atom, a saturated or unsaturated aliphatic hydrocarbon group or cyclic aliphatic hydrocarbon group which may or may not have a substituent, or an aromatic hydrocarbon group, or the same heterocyclic group as described above; $R^5$ represents hydrogen atom, or a saturated or unsaturated aliphatic hydrocarbon group or cyclic aliphatic hydrocarbon group, which may or may not have a substituent, or an aromatic hydrocarbon group, or the same heterocyclic group as described above, or the hydrocarbon group or heterocyclic group bonded together via hydroxyl group or oxygen atom; and $R^3$ and $R^4$, $R^3$ and $R^5$ or $R^4$ and $R^5$, are bonded together to form a ring), to produce optically active amines represented by the following formula (VI);

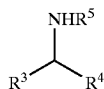

(wherein $R^3$, $R^4$ and $R^5$ are the same as described above).

Still furthermore, the present invention is to provide a method for producing optically active secondary alcohols, comprising subjecting racemic secondary alcohols or meso-type diols to hydrogen transfer reaction by using a catalyst of an optically active ruthenium-diamine complex represented by the following general formula (VII);

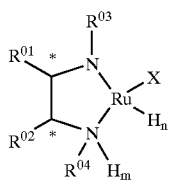

(wherein * represents an asymmetric carbon atom; $R^{01}$ and $R^{02}$ are the same or different, independently representing alkyl group, or phenyl group or cycloalkyl group which may or may not have an alkyl group; or $R^{01}$ and $R^{02}$ together form an alicyclic ring unsubstituted or substituted with an alkyl group; $R^{03}$ represents methanesulfonyl group, trifluoromethanesulfonyl group, naphthylsulfonyl group, camphor sulfonyl group, or benzenesulfonyl group which may or may not be substituted with an alkyl group, an alkoxyl group or halogen atom, alkoxycarbonyl group, or benzoyl group which may or may not be substituted with an alkyl group; $R^{04}$ represents hydrogen atom or alkyl group; X represents an aromatic compound which may or may not be substituted with an alkyl group; and m and n together represent 0 or 1).

DESCRIPTION OF THE PREFERRED EMBODIMENTS

In accordance with the present invention, the characteristic methods for producing optically active compounds and catalysts therefor as described above are provided. The detail is described below.

Firstly, the method for producing an optically active alcohol of the general formula (I) wherein $W_1$ is oxygen atom and of the general formula (II) wherein $R^2$ is OH (hydroxyl group) is described. In the formulas (I) and (II), Ra and Rb independently represent a linear or cyclic hydrocarbon or heterocyclic group which may or may not have a substituent, and the carbonyl compound represented by Ra, Rb and $W_1$ (oxygen atom) are represented by the following formula (III) as described above, and the optically active alcohol compound produced by the hydrogen transfer-type asymmetric reduction of the carbonyl compound represented by the formula (III) may satisfactorily be represented by the formula (IV).

Herein, $R^1$ represents a monocyclic or polycyclic aromatic hydrocarbon group, a saturated or unsaturated aliphatic hydrocarbon group or cyclic aliphatic hydrocarbon group, which may or may not have a substituent, or a heterocyclic group which may or may not have a substituent and contains hetero atoms such as nitrogen, oxygen, sulfur atoms and the like as atoms composing the ring. The cyclic aliphatic hydrocarbon group and heterocyclic group may satisfactorily be monocyclic or polycyclic like the aromatic hydrocarbon group. The cyclic hydrocarbon (aromatic or alicyclic) and the heterocyclic groups are of condensed series or non-condensed series if they are polycyclic.

For example, $R^1$ specifically includes aromatic monocyclic or polycyclic groups such as phenyl group, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl (cumyl), mesityl, xylyl, 1-naphthyl, 2-naphthyl, anthryl, phenanthryl, and indenyl; hetero monocyclic or polycyclic groups such as thienyl, furyl, pyranyl, xanthenyl, pyridyl, pyrrolyl, imidazolynyl, indolyl, carbazoyl, and phenanthronylyl; and ferrocenyl group.

Like these examples, the compound may satisfactorily have various substituents as the substituent, which may be hydrocarbon groups such as alkyl, alkenyl, cycloalkyl and cycloalkenyl; halogen atoms; oxygen-containing groups such as alkoxy group, carboxyl group and ester group; nitro group; amino group and the like.

Alternatively, $R^2$ represents hydrogen atom, a saturated or unsaturated aliphatic hydrocarbon group or cyclic aliphatic hydrocarbon group which may or may not have a substituent or an aromatic hydrocarbon group, or the same heterocyclic group containing hetero atoms, as described above. These are for example alkyl groups such as methyl, ethyl, propyl, butyl, pentyl, hexyl and heptyl; cycloalkyl groups such as cyclopropyl, cyclobutyl, cyclopentyl and cyclohexyl; unsaturated hydrocarbon such as vinyl and allyl; and the same as those for $R^1$. Furthermore, $R^2$ may satisfactorily include derivatives of β-keto acid with a functional group at position β. When $R^1$ and $R^2$ are bonded together to form a ring, $R^2$ is for example a saturated or unsaturated alicyclic group to form cyclic ketones, such as cyclopentanone, cyclohexanone, cycloheptane, cyclopentenone, cyclohexenone, and cycloheptenone; and saturated and unsaturated alicyclic groups with a linear or cyclic hydrocarbon substituent group containing alkyl group, aryl group, unsaturated alkyl group and hetero atom on individual carbons.

According to the method for producing optically active alcohol compounds through asymmetric reduction of carbonyl compounds, an asymmetric reduction catalyst system of a transition metal complex and an optically active nitrogen-containing compound is used for the asymmetric reduction.

As the metal catalyst, then, use is made of various transition metals because they have ligands; particularly preferably; use is made of a transition metal complex represented by the following general formula (a);

$$MX_mL_n \qquad (a)$$

(wherein M represents transition metals of group VIII, such as iron, cobalt, nickel, ruthenium, rhodium, iridium, osmium, palladium and platinum; X represents hydrogen, halogen atom, carboxyl group, hydroxy group and alkoxy group and the like; L represents neutral ligands such as aromatic compounds and olefin compounds; and m and n represent an integer). As the transition metals in these transition metal catalysts, ruthenium is one of preferable examples.

When the neutral ligands are aromatic compounds, a monocyclic aromatic compound represented by the following general formula (b) can be illustrated. Herein, $R^0$'s are all the same or different substituent groups, including hydrogen atom, a saturated or unsaturated hydrocarbon group, allyl group or a functional group containing hetero atoms. For example, $R^0$ includes alkyl groups such as methyl, ethyl, propyl, isopropyl, butyl, t-butyl, pentyl, hexyl, and heptyl; cycloalkyl groups such as cyclopropyl, cyclobutyl, cyclopentyl, and cyclohexyl; groups of unsaturated hydrocarbons such as benzyl, vinyl, and allyl; functional groups containing hetero atoms, such as hydroxyl group, alkoxy group, and alkoxycarbonyl group. The number of the substituents $R^0$'s is an appropriate number of 1 to 6, and the substituents can occupy any position.

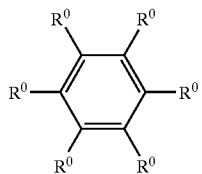

(b)

The transition metal catalysts of the group VIII and the like are used to an amount variable, depending on the size, mode and economy of the reactor, but the catalysts may satisfactorily be used within a molar ratio range of approximately 1/100 to 1/100,000, preferably 1/500 to 1/5,000 to the reaction substrate carbonyl compound.

In accordance with the present invention, use is made of optically active nitrogen-containing compounds in the asymmetric catalyst system, and it is possibly assumed that the compounds are present as asymmetric ligands to the transition metal complexes or serve as such. For more easily understandable expression, such optically active nitrogen-containing compounds may also be illustrated as "optically active amine compounds". The optically active amine compounds are optically active diamine compounds represented by the following general formula (c);

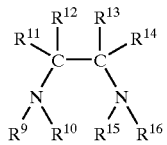

(c)

(wherein $R^9$, $R^{10}$, $R^{15}$ and $R^{16}$ are independently hydrogen, a saturated or unsaturated hydrocarbon group, urethane group or sulfonyl group; $R^{11}$, $R^{12}$, $R^{13}$ and $RL^{14}$ are the same or different so that the carbon bonded with these substituent groups might occupy the asymmetric center, including hydrogen atom, an aromatic group, a saturated or unsaturated aliphatic hydrocarbon group or cyclic aliphatic hydrocarbon group; even in this case, the aromatic or cyclic aliphatic group may be monocyclic or polycyclic; the polycyclic aromatic group is any of condensed series or non-condensed series; and furthermore, any one of $R^{11}$ and $R^{12}$ and any one of $R^{13}$ and $R^{14}$ are bonded together to form a ring. For example, such compounds include optically active diamine compounds such as optically active 1,2-diphenylethylenediamine, 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphthyldiamine, 1-isobutyl-2,2-dinaphthylethylenediamine, 1-isopropyl-2,2-dinaphthylethylenediamine and the like. Additionally, optically active diamine compounds wherein any one or two of substituents $R^9$ through $R^{15}$ are sulfonyl group, acyl group or urethane group are illustrated. Preferably, furthermore, use may be made of optically active diamine compounds with one sulfonyl group. Furthermore, the optically active diamine (compounds) for potential use are not limited to the illustrated optically active ethylenediamine derivatives, and use may be made of optically active propanediamine, butanediamine, and phenylenediamine derivatives.

As the optically active amine compounds, use is made of optically active amino alcohol compounds represented by the following general formula (d).

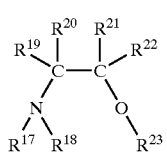

(d)

Herein, at least one of $R^{17}$ and $R^{18}$ is hydrogen atom, and the remaining one is hydrogen atom, a saturated or unsaturated hydrocarbon group, urethane group or sulfonyl group; $R^{19}$, $R^{20}$, $R^{21}$ and $R^{22}$ are the same or different so that the carbon bonded with these substituent groups might occupy the asymmetric center, including hydrogen atom, a monocyclic or polycyclic aromatic group, a saturated or unsaturated aliphatic hydrocarbon group, and a cyclic aliphatic hydrocarbon group; $R^{23}$ represents hydrogen atom, a monocyclic or polycyclic aromatic group, a saturated or unsaturated aliphatic hydrocarbon group and cyclic aliphatic hydrocarbon group. Furthermore, any one of $R^{19}$ and $R^{20}$ and any one of $R^{21}$ and $R^{22}$ may satisfactorily be bonded together to form a ring. Additionally, any one of $R^{17}$ and $R^{18}$ and any one of $R^{20}$ and $R^{21}$ may satisfactorily be bonded together to form a ring. More specifically, use may satisfactorily be made of optically active amino-alcohols shown in the examples described below.

As the optically active amine compounds, furthermore, use may be made of aminophosphine compounds represented by the following general formula (e);

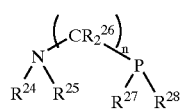

(e)

Herein, $R^{24}$ and $R^{25}$ are hydrogen atom, a saturated or unsaturated hydrocarbon group, urethane group, sulfonyl group and acyl group; $(CR_2^{26})_n$ are the same or different so that the carbon bonded with these substituent groups might occupy the asymmetric center, including hydrogen atom, a monocyclic or polycyclic aromatic group, a saturated or unsaturated hydrocarbon group, and a cyclic hydrocarbon group; $R^{27}$ and $R^{28}$ represent hydrogen atom, and a saturated or unsaturated hydrocarbon group. More specifically, use may be made of the optically active aminophosphines shown in the examples.

The optically active amine compounds as illustrated above are generally used for example at an amount at approximately 0.5 to 20 equivalents, and preferably used for example within a range of 1 to 4 equivalents, to the transition metal complex.

In the aforementioned catalyst system to be used for the method for producing optically active alcohols through asymmetric reduction of carbonyl compounds, advantageously, an additional basic substance is advantageously present currently.

Such basic substance includes for example metal salts or quaternary ammonium compounds represented by the following formula (f);

M¹Y (f)

(wherein $M^1$ represents an alkali metal or alkali earth metal; and Y represents hydroxy group, alkoxy group, mercapto group and naphthyl group). More specifically, $M^1$ includes KOH, $KOCH_3$, $KOCH(CH_3)_2$, $KOC(CH_3)_3$, $KC_{10}H_8$, LiOH, $LiOCH_3$, $LiOCH(CH_3)_2$, $LiOC(CH_3)_3$, NaOH, $NaOCH_3$, $NaOCH(CH_3)_2$, $NaC_{10}H_8$, $NaOC(CH_3)_3$, and the like. Furthermore, quaternary ammonium salts may be used satisfactorily.

The amount of the base to be used is generally about 0.5 to 50 equivalents, preferably 2 to 10 equivalents to the transition metal complex.

As has been described above, the basic substance is used for smoothly progressing the asymmetric reduction. Therefore, the base is an important component so as to give optically active alcohol compounds with a high a optical purity.

For the method for producing optically active alcohol compounds through hydrogen transfer-type asymmetric reduction in accordance with the present invention, it is inevitable to use hydrogen-donating organic or inorganic compounds. By these are meant compounds capable of donating hydrogen via thermal action or catalytic action, and the types of such hydrogen-donating compounds are not specifically limited, but preferably include alcohol compounds such as methanol, ethanol, 1-propanol, 2-propanol, butanol, and benzyl alcohol; formic acid and salts thereof, for example those in combination with amines; an unsaturated hydrocarbon and heterocyclic compounds having in part a saturated carbon bond, such as tetralin and decalin; hydroquinone or phosphorous acid or the like. Among them, alcohol compounds are preferable, and 2-propanol and formic acid are more preferable. The amount of an organic compound to be used and function as a hydrogen source is determined on the basis of the solubility and economy of the reaction substrate. Generally, the substrate concentration may be about 0.1 to 30% by weight for some type of substrates, but preferably, the concentration is 0.1 to 10% by weight. When using formic acid and a combination of formic acid with amine as a hydrogen source, no solvent is necessarily used. If any solvent is intentionally used, use is made of aromatic compounds such as toluene and xylene; halogen compounds such as dichloromethane, organic compounds such as DMSO, DMF or acetonitrile.

According to the method for producing optically active alcohol compounds in accordance with the present invention, hydrogen pressure is essentially not required, but depending on the reaction conditions, hydrogen pressure may satisfactorily be loaded. Even if hydrogen pressure is loaded, the pressure may satisfactorily be about 1 atom. to several atm. because the catalyst system is extremely highly active.

The reaction temperature is about −20° C. to 100° C. from the economical standpoint. More practically, the reaction can be carried out around room temperature of 25 to 40° C. The reaction time varies, depending on the reaction conditions such as the concentration of a reaction substrate, temperature and pressure, but the reaction is on completion from several minutes to 100 hours.

For use, the metal complex is preliminarily mixed with an optically active amine compound as an optically active nitrogen-containing compound, but an a chiral metal complex may be synthesized preliminarily by the following method, and the resulting complex may be used.

More specifically, the method comprises adding an optically active amine compound, a transition metal complex and a complex into for example alcohol, and subsequently heating the resulting mixture in an inactive gas under agitation. Then, the resulting solution is cooled and treated under reduced pressure, prior to recrystallization, to prepare an asymmetric complex catalyst.

Together with the method for producing optically active alcohol compounds as described above, the present invention is to provide a method for producing optically active amine compounds represented by the general formula (II) as described above, wherein $W_1$ is OH, $NH_2$, NH-Rc, NH-OH or NH-O-Rd, comprising asymmetric reduction by using an imine compound represented by the general formula (I) wherein $W_1$ is NH, N-Rc, N-OH or N-O-Rd (Rc and Rd independently represent a linear or cyclic hydrocarbon group which may or may not have a substituent, or a heterocyclic group).

More specifically, for example, the present invention is to provide a method for producing an optically active amine compound of the following formula (VI), comprising asymmetric reduction of an imine compound of the following formula (V).

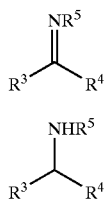

(V)

(VI)

Herein, $R^3$ and $R^4$ are almost the same as those in the case of the carbonyl compounds and the optically active alcohol compounds of the formulas (III) and (IV), respectively.

For example, $R^3$ is an aromatic monocyclic or polycyclic hydrocarbon group, unsubstituted or substituted, a saturated or unsaturated aliphatic hydrocarbon group or cyclic hydrocarbon group, unsubstituted or substituted, or a hetero monocyclic or polycyclic group containing hetero atoms such as nitrogen, oxygen, sulfur atoms and the like; more specifically, $R^3$ includes aromatic monocyclic or polycyclic hydrocarbon groups such as phenyl group, 2-methyphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methyphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl, and indenyl groups; hetero monocyclic or polycyclic groups such as thienyl, furyl, pyranyl, xanthenyl, pyridyl, pyrrolyl, imidazolyl, indolyl, carbazoyl, and phenanthronylyl; and ferrocenyl group. Like these examples, $R^3$ may contain any of various substituents, which may satisfactorily be hydrocarbon groups such as alkyl, alkenyl, cycloalkyl, and cycloalkenyl; halogen atom; oxygen-containing groups such as alkoxy group, carboxyl group and ester group; nitro group; cyano group and the like.

Furthermore, $R^4$ represents hydrogen atom, a saturated or unsaturated hydrocarbon group, aryl group, hetero atom-containing functional groups, including for example alkyl groups such as methyl, ethyl, propyl, butyl, pentyl, hexyl, and heptyl; cycloalkyl groups such as cyclopropyl, cyclobutyl, cyclopentyl, and cyclohexyl; unsaturated hydrocarbons such as vinyl and allyl; and the same as those for R1. Additionally, $R^5$ represents hydrogen atom, a saturated and unsaturated hydrocarbon group, aryl group, a hetero atom-containing heterocyclic group, or the hydrocarbon group or heterocyclic group bonded together via hydroxyl group or oxygen atom, including for example alkyl groups such as methyl, ethyl, propyl, butyl, pentyl, hexyl and heptyl; cycloalkyl groups such as cyclopropyl, cyclobutyl, cyclopentyl, and cyclohexyl; unsaturated hydrocarbon groups such as benzyl, vinyl and allyl; hydroxyl group; alkyl ether groups; aryl ether groups; and the like. Furthermore, a saturated or unsaturated cyclic imine compound formed by bonding together $R^3$ and $R^4$, $R^3$ and $R^5$ or $R^4$ and $R^5$, is illustrated.

Non-cyclic imine compounds can be synthesized readily from the corresponding ketone and amines. In this case, the syn-form and anti-form or a mixture enriched with either one of these syn- and anti-forms may be used satisfactorily, but a purified product of the mixture may be used singly or a mixture thereof with another imine compound may also be used.

Even by the method for producing optically active amine compounds, like the method for producing optically active alcohol compounds, use is made of an asymmetric reduction catalyst composed of a transition metal complex and an optically active nitrogen-containing compound. In the transition metal complex among them, various transition metals with ligands are used, and particularly preferably, use is made of those similar to a transition metal complex represented by the general formula (a);

$$MXmLn \quad (a)$$

(wherein M is a transition metal of group VIII, such as iron, cobalt, nickel, ruthenium, rhodium, iridium, osmium, palladium and platinum; X represents hydrogen, halogen atom, carboxyl group, hydroxy group and alkoxy group and the like; L represents neutral ligands such as aromatic compounds and olefin compounds; m and n represent an integer). The transition metal in the transition metal complex is preferably rare metal, and specifically, ruthenium is one of preferable examples.

Like the method for producing optically active alcohols, a monocyclic aromatic compound represented by the general formula (b) is illustrated for the aromatic compound as the neutral ligand. Herein, $R^0$'s are the same or different substituent-groups, representing hydrogen atom, a saturated or unsaturated hydrocarbon group, aryl group, and functional groups containing hetero atoms, for example alkyl groups such as methyl, ethyl, propyl, isopropyl, butyl, t-butyl, pentyl, hexyl, and heptyl; cycloalkyl groups such as cyclopropyl, cyclobutyl, cyclopentyl and cyclohexyl; unsaturated hydrocarbon groups such as benzyl, vinyl, and allyl; hetero atom-containing functional groups such as hydroxyl group, alkoxy group and alkoxycarbonyl group. The number of the substituents $R^0$'s is an optional number of 1 to 6, and the substituents each can occupy any position.

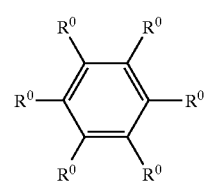

(b)

The transition metal catalysts are used at an amount variable, depending on the size, mode and economy of the reactor, but the catalysts may satisfactorily be used within a molar ratio range of approximately 1/100 to 1/100,000, preferably 1/200 to 1/5,000 to the reaction substrate imine compound.

According to the method for producing optically active amine compounds in accordance with the present invention, additionally, use is made of optically active nitrogen-containing compounds in the asymmetric catalyst system, and it is possibly assumed that the compounds may be present as asymmetric ligands in the transition metal complexes or may serve as such. For more easily understandable expression, such optically active nitrogen-containing compounds are illustrated as "optically active amine compounds". As described above, the optically active amine compounds are optically active diamine compounds represented for example by the following general formula (c);

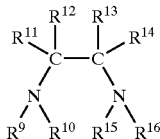

(c)

(wherein $R^9$, $R^{10}$, $R^{15}$, and $R^{16}$ are independently hydrogen, a saturated or unsaturated hydrocarbon group, urethane group or sulfonyl group; $R^{11}$, $R^{12}$, $R^{13}$ and $R^{14}$ are the same or different so that the carbon bonded with these substituent groups might occupy the asymmetric center, including hydrogen atom, aromatic monocyclic and polycyclic groups, a saturated or unsaturated hydrocarbon group or cyclic hydrocarbon group; even in this case, the aromatic, or cyclic, or cyclic aliphatic group may be monocyclic or polycyclic; the polycyclic aromatic group is any of condensed series or non-condensed series; and furthermore, any one of $R^{11}$ and $R^{12}$ may satisfactorily form a ring. For example, such compounds include optically active diamine compounds such as optically active 1,2-diphenylethylenediamine, 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2-dinaphthylethylenediamine, 1-isobutyl-2,2-dinaphthylethylenediamine, 1-isopropyl-2,2-dinaphthylethylenediamine and the like. Additionally, optically active diamine compounds wherein any one or two of substituents $R^9$ through $R^{15}$ are sulfonyl group, acyl group or urethane group may also be used. Preferably, furthermore, use may be made of optically active diamine compounds with one sulfonyl group. Furthermore, optically active diamine (compounds) to be possibly used are not limited to the illustrated optically active ethylenediamine derivatives, and use may be made of optically active propanediamine, butanediamine, and phenylenediamine derivatives.

As the optically active amine compound, use is made of an optically active amino alcohol compound represented by the following general formula (d);

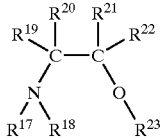

(d)

Herein, at least one of $R^{17}$ and $R^{19}$ is hydrogen atom, and the remaining one is hydrogen atom, a saturated or unsaturated hydrocarbon group, urethane group or sulfonyl group; $R^{19}$, $R^{20}$, $R^{21}$ and $R^{22}$ are the same or different so that the carbon bonded with these substituent groups might occupy the asymmetric center, including hydrogen atom, an aromatic monocyclic or polycyclic group, a saturated or unsaturated hydrocarbon group, or a cyclic hydrocarbon group; $R^{23}$ represents hydrogen atom, an aromatic monocyclic or polycyclic group, a saturated or unsaturated hydrocarbon group and a cyclic hydrocarbon group. Furthermore, any one of $R^{19}$ and $R^{20}$ and any one of $R^{21}$ and $R^{22}$ may satisfactorily be bonded together to form a ring, or any one of $R^{17}$ and $R^{18}$ and any one of $R^{20}$ and $R^{21}$ may satisfactorily be bonded together to form a ring. More specifically, use is made of optically active amino alcohols shown in the examples described below.

As the optically active amine compound, furthermore, use is made of aminophosphine compound represented by the following general formula (e).

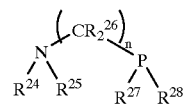

(e)

Herein, $R^{24}$ and $R^{25}$ are hydrogen atom, a saturated or unsaturated hydrocarbon group, urethane group, sulfonyl group and acyl group; $(CR_2^{16})_n$ are the same or different so that the carbon bonded with these substituent groups might occupy the asymmetric center, including hydrogen atom, an aromatic monocyclic or polycyclic group, a saturated or unsaturated hydrocarbon group, and a cyclic hydrocarbon group; $R^{27}$ and $R^{28}$ represent hydrogen atom, a saturated or unsaturated hydrocarbon group, and allyl group. More specifically, use is made of the optically active aminophosphines shown in the examples.

The optically active amine compounds as illustrated above are used at an amount for example of approximately 0.5 to 20 equivalents, and preferably within a range of 1 to 2 equivalents, to the transition metal complex.

The transition metal catalyst to be used as the catalyst as described above and the optically active amine compound are essential components to progress the asymmetric reduction in a smooth manner thereby attaining a higher asymmetric yield, and amine compounds at a higher optical purity cannot be recovered at a sufficiently high reaction activity, if either one of the two is eliminated.

For the method for producing optically active amines through hydrogen transfer-type asymmetric reduction in accordance with the present invention, the presence of a hydrogen-donating organic or inorganic compound is indispensable. These compounds mean compounds capable of donating hydrogen through thermal action or catalytic action, and the types of these hydrogen-donating compounds are not limited, but preferably include alcohol compounds such as methanol, ethanol, 1-propanol, 2-propanol, butanol, and benzyl alcohol; formic acid and salts thereof, such as those in combination with amines; unsaturated hydrocarbons and heterocyclic compounds having saturated carbon bonds in part, such as tetralin and decalin; hydroquinone or phosphorous acid or the like. Among them, alcohol compounds are preferable, and 2-propanol is more preferable. The amount of an organic acid to be used as a hydrogen source is determined, depending on the solubility and economy of the reaction substrate. Generally, the substrate is used at a concentration of approximately 0.1 to 30% by weight, depending on the type of the substrate to be used, and is preferably at a concentration of 0.1 to 10% by weight. When using formic acid and a combination of formic acid with amine as a hydrogen source, no solvent is necessarily used, but use may satisfactorily be made of aromatic compounds such as toluene and xylene; halogen compounds such as dichloromethane, or organic compounds such as DMSO, DMF or acetonitrile, if it intended to use any solvent.

Hydrogen pressure is essentially not required, but depending on the reaction conditions, hydrogen pressure may satisfactorily be loaded. Even if hydrogen pressure is loaded, the pressure may satisfactorily be about 1 atm to 50 atm.

The reaction temperature is about −20° C. to 100° C. from the economical standpoint. More practically, the reaction can be carried out around room temperature of 25 to 40° C. The reaction time varies, depending on the reaction conditions such as the concentration of a reaction substrate, temperature and pressure, but the reaction is on completion from several minutes to 100 hours.

The metal complex to be used in accordance with the present invention is preliminarily mixed with an optically active amine compound, but an asymmetric metal complex may be preliminarily synthesized by the following method, and the resulting complex may be used.

More specifically, for example, a method is illustrated, comprising suspending a ruthenium-arene complex, an optically active amine compound and triethylamine in 2-propanol, heating the resulting mixture in argon or nitrogen gas stream under agitation, and cooling then the resulting reaction mixture, from which the solvent is then removed, and re-crystallizing the resulting mixture in an alcohol solvent to prepare an asymmetric complex.

The catalyst system to be used for the hydrogen transfer-type asymmetric reduction in accordance with the present invention is very characteristic and has never been known up to now.

The optically active ruthenium-diamine complex represented by the following formula (VII) as described above as one metal complex composed of a transition metal and an optically active nitrogen-containing compound ligand is useful as a catalyst for producing optically active secondary alcohol compounds, comprising subjecting racemic secondary alcohol or meso-type diols to hydrogen transfer reaction, and therefore, the complex draws higher attention.

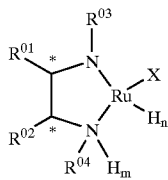

(VII)

In the formula, * represents an asymmetric carbon atom; $R^{01}$ and $R^{02}$ are the same or different, independently representing alkyl group, or phenyl group or cycloalkyl group which may or may not have an alkyl group; or $R^{01}$ and $R^{02}$ together form an alicyclic ring unsubstituted or substituted with an alkyl group; $R^{03}$ represents methanesulfonyl group, trifluoromethanesulfonyl group, naphthylsulfonyl group, camphor sulfonyl group, or benzenesulfonyl group which may or may not be substituted with an alkyl group, an alkoxyl group or halogen atom, alkoxycarbonyl group, or benzoyl group which may or may not be substituted with an alkyl group; $R^{04}$ represents hydrogen atom or alkyl group; X represents an aromatic compound which may or may not be substituted with an alkyl group; and m and n simultaneously represent 0 or 1.

For more description of the optically active ruthenium-diamine complex of the formula (VII), the aromatic compound which may or may not have an alkyl group represented by X, for example alkyl groups with C1 to C4, means for example benzene, toluene, xylene, mesitylene, hexamethylbenzene, ethylbenzene, tert-butylbenzene, p-cymene, and cumene and preferably includes benzene, mesitylene and p-cymene.

$R^{01}$ and $R^{02}$ represent a linear or branched alkyl group, if they represent an alkyl group, for example alkyl groups with C1 to C4. More specifically, the alkyl group includes methyl, ethyl, n-propyl, isopropyl, n-, iso-, sec- and tert-butyl. More preferably, the group includes methyl, ethyl, n-propyl or iso-propyl.

If $R^{01}$ and $R^{02}$ are bonded together to form an alicyclic group, the group may satisfactorily be a C5 to C7-membered ring. The alkyl group which may or may not be a substituent therefor, for example alkyl substituent group with C1 to C4, includes methyl group, ethyl group, n-propyl group, isopropyl group, and n-, iso-, sec- and tert-butyl groups. Preferably, the alkyl group is methyl.

$R^1$ and $R^2$ as phenyl group wherein $R^{01}$ and $R^{02}$ may have an alkyl group, for example methyl group, specifically include phenyl, o-, m- and p-tolyl groups.

$R^{01}$ and $R^{02}$ representing cycloalkyl group contain carbon atoms in 5 to 6-membered rings, preferably including cyclopentyl or cyclohexyl.

In more preferable examples, $R^{01}$ and $R^{02}$ are independently phenyl or $R^{01}$ and $R^{02}$ together mean tetramethylene (-(CH$_2$)$_4$-).

$R^{03}$ represents methanesulfonyl group, trifluoromethanesulfonyl group, naphthylsulfonyl group, camphor sulfonyl group, or benzenesulfonyl group which may or may not be substituted with alkyl group, for example alkyl group with C1 to C3, alkoxy group for example alkoxy group with C1 to C3, or halogen atom, or benzoyl group which may or may not be substituted with alkyl group, for example C1 to C4 alkoxycarbonyl groups, or alkyl group, for example C1 to C4 alkyl group.

More specifically, $R^{03}$ representing benzenesulfonyl group which may or may not be substituted with C1 to C3 alkyl group, C1 to C3 alkoxyl group or halogen atom, includes benzenesulfonyl, o-, m- and p-toluenesulfonyl, o-, m-, and p-ethylbenzenesulfonyl, o-, m-, and p-methoxybenzenesulfonyl, o-, m-, and p-ethoxybenzenesulfonyl, o-, m-, and p-chlorobenzenesulfonyl, 2, 4, 6-trimethylbenzenesulfonyl, 2,4,6-triisopropylbenzenesulfonyl, p-fluorobenzenesulfonyl, and pentafluorobenzenesulfonyl, and more preferably includes benzenesulfonyl or p-toluenesulfonyl. Specifically, $R^{03}$ representing C1 to C4 alkoxycarbonyl groups includes methoxycarbonyl, ethoxycarbonyl, isopropyloxycarbonyl, and tert-butoxycarbonyl, preferably including methoxycarbonyl or tert-butoxycarbonyl. $R^{03}$ representing benzoyl group which may or may not be substituted with C1 to C4 alkyl groups specifically includes benzoyl, o-, m-, and p-methylbenzoyl, o-, m-, and p-ethylbenzoyl, o-, m-, and p-isopropylbenzoyl, and o-, m-, and p-tert-butylbenzoyl, preferably including benzoyl or p-methylbenzoyl.

In the most preferable example, $R^{03}$ is methanesulfonyl, trifluoromethanesulfonyl, benzenesulfonyl or p-toluenesulfonyl.

$R^{04}$ representing hydrogen atom or alkyl group, for example C1 to C4 alkyl groups, specifically includes for example hydrogen, methyl, ethyl, n-propyl, isopropyl, n-, iso-, sec- and tert-butyl, and more preferably includes hydrogen atom or methyl group.

The optically active ruthenium-diamine complex is used for the method for producing optically active secondary alcohols from ketones as descried above in accordance with the present invention, and in this case, the racemic secondary alcohols as the raw material compounds in accordance with the present invention are illustrated by the following formula (VIII). It is needless to say that the racemic alcohols are not limited to those represented by the formula.

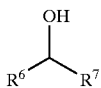
(VIII)

R[4] represents an aromatic monocyclic or polycyclic hydrocarbon group, unsubstituted or substituted or a hetero monocyclic or polycyclic group containing hetero atoms including nitrogen, oxygen, sulfur atoms and the like, specifically representing aromatic monocyclic or polycyclic groups such as phenyl group, 2-methylphenyl, 2-ethylphenyl, 2-isopropylphenyl, 2-tert-butylphenyl, 2-methoxyphenyl, 2-chlorophenyl; 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenanthryl, and indenyl; hetero monocyclic or polycyclic groups such as thienyl, furyl, pyranyl, xanthenyl, pyridyl, pyrrolyl, imidazolyl, indolyl, carbazoyl, and phenthronylyl; and ferrocenyl group. Furthermore, R[7] represents hydrogen atom, a saturated or unsaturated hydrocarbon group, or a functional group containing hetero atoms, including for example alkyl groups such as methyl, ethyl, propyl, isopropyl, butyl, pentyl, hexyl, and heptyl; cycloalkyl groups such as cyclopropyl, cyclobutyl, cyclopentyl, and cyclohexyl; and unsaturated hydrocarbons such as benzyl, vinyl, and allyl. R[6] and R[7] may be bonded together to form a ring, and in this case, R[7] includes for example a saturated or unsaturated alicyclic group giving a cyclic ketone such as cyclopentanone, cyclohexanone, cycloheptane, cyclopentenone, cyclohexenone, and cycloheptenone; or a saturated and unsaturated alicyclic group with a substituent group having an alkyl group, an aryl group, a unsaturated alkyl group or a linear or cyclic hydrocarbon group on each of the individual carbons.

Additionally, the meso-type diols are represented for example by the following formula (IX).

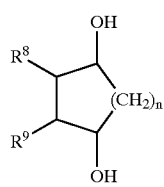
(IX)

It is needless to say that the meso-diols are not limited to them.

In this case, R[8] and R[9] are the same and represent a saturated or unsaturated hydrocarbon group which may or may not have a substituent group, or R[8] and R[9] may be bonded together to form a saturated or unsaturated alicyclic group which may or may not have a substituent group.

More specifically, the ruthenium-diamine complex of the present invention is for example such that m and n are simultaneously zero in the formula (VII). Herein, η is used to represent the number of carbon atoms bonded to a metal in unsaturated ligands, and therefore, hexahapto (six carbon atoms bonded to metal) is represented by $\eta^6$; p-Ts represents p-toluenesulfonyl group; Ms represents methanesulfonyl group; and Tf represents trifluoromethanesulfonyl group.

Ru[(S, S)-p-TsNCH($C_6H_5$)CH($C_6H_5$)NH]($\eta^6$-benzene)(((S, S)-N-p-toluenesulfonyl-1,2-diphenylethylenediamine) ($\eta^6$-benzene)ruthenium)

Ru[(R, R)-p-TsNCH($C_6H_5$)CH($C_6H_5$)NH]($\eta^6$-benzene) (((R, R)-N-p-toluenesulfonyl-1,2-diphenylethylenediamine) ($\eta^6$-benzene) ruthenium)

Ru[(S, S)-p-TsNCH($C_6H_5$)CH($C_6H_5$)NH]($\eta^6$-p-cymene) (((S, S)-N-p-toluenesulfonyl-1,2-diphenylethylenediamine) ($\eta^6$-p-cymene)ruthenium)

Ru[(R, R)-p-TsNCH($C_6H_5$)CH($C_6H_5$)NH]($\eta^6$-p-cymene) (((R, R)-N-p-toluenesulfonyl-1, 2-diphenylethylenediamine) ($\eta^6$-p-cymene)ruthenium)

Ru[(S, S)-p-TsNCH($C_6H_5$)CH($C_6H_5$)NH]($\eta^6$-mesitylene) (((S, S)-N-p-toluenesulfonyl-1,2-diphenylethylenediamine) ($\eta^6$-mesitylene)ruthenium)

Ru[(R, R)-p-TsNCH($C_6H_5$)CH($C_6H_5$)NH]($\eta^6$-mesitylene) (((R, R)-N-p-toluenesulfonyl-1,2-diphenylethylenediamine)($\eta^6$-mesitylene)ruthenium)

Ru[(S, S)-MsNCH($C_6H_5$)CH($C_6H_5$)NH]($\eta^6$-benzene)(((S, S)-N-methanesulfonyl-1,2-diphenylethylenediamine) ($\eta^6$-benzene)ruthenium)

Ru[(R, R)-MsNCH($C_6H_5$)CH($C_6H_5$)NH]($\eta^6$-benzene)(((R, R)-N-methanesulfonyl-1,2-diphenylethylenediamine) ($\eta^6$-benzene)ruthenium)

Ru[(S, S)-MsNCH($C_6H_5$)CH($C_6H_5$)NH]($\eta^6$-p-cymene) (((S, S)-N-methanesulfonyl-1,2-diphenylethylenediamine)($\eta^6$-p-cymene)ruthenium)

Ru[(R, R)-MSNCH($C_6H_5$)CH($C_6H_5$)NH]($\eta^6$-p-cymene) (((R, R)-N-methanesulfonyl-1,2-diphenylethylenediamine)($\eta^6$-p-cymene)ruthenium)

Ru[(S, S)-MSNCH($C_6H_5$)CH($C_6H_5$)NH]($\eta^6$-mesitylene) (((S, S)-N-methanesulfonyl-1,2-diphenylethylenediamine)($\eta^6$-mesitylene)ruthenium)

Ru[(R, R)-MsNCH($C_6H_5$)CH($C_6H_5$)NH]($\eta^6$-mesitylene) (((R, R)-N-methanesulfonyl-1,2-diphenylethylenediamine)($\eta^6$-mesitylene)ruthenium)

Ru[(S, S)-TfNCH($C_6H_5$)CH($C_6H_5$)NH]($\eta^6$-benzene)(((S S)-N-trifluoromethanesulfonyl-1,2-diphenylethylenediamine)($\eta^6$-benzene)ruthenium)

Ru[(R, R)-TfNCH($C_6H_5$)CH($C_6H_5$)NH]($\eta^6$-benzene) ((R, R)-N-trifluoromethanesulfonyl-1, 2-diphenylethylenediamine)($\eta^6$-benzene)ruthenium)

RU[(S, S)-TfNCH($C_6H_5$)CH($C_6H_5$)NH]($\eta^6$-p-cymene)(((S, S)-N-trifluoromethanesulfonyl-1,2-diphenylethylenediamine)($\eta^6$-p-cymene)ruthenium)

Ru[(R, R)-TfNCH($C_6H_5$)CH($C_6H_5$)NH]($\eta^6$-p-cymene) (((R, R)-N-trifluoromethanesulfonyl-1,2-diphenylethylenediamine)($\eta^6$-p-cymene)ruthenium)

Ru[(S, S)-TfNCH($C_6H_5$)CH($C_6H_5$)NH]($\eta^6$-mesitylene) (((S, S)-N-trifluoromethanesulfonyl-1,2-diphenylethylenediamine)($\eta^6$-mesitylene)ruthenium)

Ru[(R, R)-TfNCH($C_6H_5$)CH($C_6H_5$)NH]($\eta^6$-mesitylene) (((R, R)-N-trifluoromethanesulfonyl-1,2-diphenylethylenediamine)($\eta^6$-mesitylene)ruthenium)

Ru[(S, S)-$C_6H_5SO_2$NCH($C_6H_5$)CH($C_6H_5$)NH]($\eta^6$-benzene)(((S, S)-N-benzenesulfonyl-1,2-diphenylethylenediamine)($\eta^6$-benzene) ruthenium)

Ru[(R, R)-$C_6H_5SO_2$NCH($C_6H_5$)CH($C_6H_5$)NH]($\eta^6$-benzene)(((R, R)-N-benzenesulfonyl-1,2-diphenylethylenediamine)($\eta^6$-benzene) ruthenium)

Ru[(S, S)-$C_6H_5SO_2$NCH($C_6H_5$)CH($C_6H_5$)NH]($\eta^6$-p-cymene)(((S, S)-N-benzenssulfonyl-1,2-diphenylethylenediamine)($\eta^6$-p-cymene)ruthenium)

Ru[(R, R)-$C_6H_5SO_2$NCH($C_6H_5$)CH($C_6H_5$)NH]($\eta^6$-p-cymene)(((R, R)-N-benzenesulfonyl-1,2-diphenylethylenediamine)($\eta^6$-p-cymene)ruthenium)

Ru[(S, S)-$C_6H_5SO_3$NCH($C_6H_5$)CH($C_6H_5$)NH]($\eta^6$-mesitylene)(((S, S)-N-benzenesulfonyl-1,2-diphenylethylenediamine)($\eta^6$-mesitylene)ruthenium)

Ru[(R, R)-$C_6H_5SO_2$NCH($C_6H_5$)CH($C_6H_5$)NH]($\eta^6$-mesitylene)(((R, R)-N-benzenesulfonyl-1,2-diphenylethylenediamine)($\eta^6$-mesitylene)ruthenium)

Ru[(S, S)-N-p-Ts-1,2-cyclohexanediamine](η⁶-benzene) (((S, S)-N-p-toluenesulfonyl-1,2-cyclohexanediamine) (η⁶-benzene)ruthenium)
Ru[(R, R)-N-p-Ts-1,2-cyclohexanediamine](η⁶-benzene) (((R, R)-N-p-toluenesulfonyl-1,2-cyclohexanediamine) (η⁶-benzene)ruthenium)
Ru[(S, S)-N-p-Ts-1,2-cyclohexanediamine](η⁶-p-cymene) (((S, S)-N-p-toluenesulfonyl-1,2-cyclohexanediamine) (η⁶-p-cymene)ruthenium)
Ru[(R, R)-N-p-Ts-1,2-cyclohexanediamine](η⁶-p-cymene) (((R, R)-N-p-toluenesulfonyl-1,2-cyclohexanediamine) (η⁶-p-cymene)ruthenium)
Ru[(S, S)-N-p-Ts-1,2-cyclohexanediamine](η⁶-mesitylene) (((S, S)-N-p-toluenesulfonyl-1,2-cyclohexanediamine) (η⁶-mesitylene)ruthenium)
Ru[(R, R)-N-p-Ts-1,2-cyclohexanediamine](η⁶-mesitylene) (((R, R)-N-p-toluenesulfonyl-1,2-cyclohexanediamine) (η⁶-mesitylene)ruthenium)
Ru[(S, S)-N-Ms-1,2-cyclohexanediamine](η⁶-benzene) (((S, S)-N-methanesulfonyl-1,2-cyclohexanediamine) (η⁶-benzene)ruthenium)
Ru[(R, R)-N-Ms-1,2-cyclohexanediamine](η⁶-benzene) ((R, R)-N-methanesulfonyl-1,2-cyclohexanediamine)(η⁶-benzene) ruthenium)
Ru[(S, S)-N-Ms-1,2-cyclohexanediamine](η⁶-p-cymene) (((S, S)-N-methanesulfonyl-1,2-cyclohexanediamine) (η⁶-p-cymene)ruthenium)
Ru[(R, R)-N-Ms-1,2-cyclohexanediamine](η⁶-p-cymene) (((R, R)-N-methanesulfonyl-1,2-cyclohexanediamine) (η⁶-p-cymene)ruthenium)
Ru[(S, S)-N-Ms-1,2-cyclohexanediamine](η⁶-mesitylene) ((S, S)-N-methanesulfonyl-1,2-cyclohexanediamine)(η⁶-mesitylene)ruthenium)
Ru[(R, R)-N-Ms-1,2-cyclohexanediamine](η⁶-mesitylene) (((R, R)-N-methanesulfonyl-1,2-cyclohexanediamine) (η⁶-mesitylene)ruthenium)
Ru[(S, S)-N-Tf-1,2-cyclohexanediamine](η⁶-benzene)(((S, S)-N-trifluoromethanesulfonyl-1,2-cyclohexanediamine) (η⁶-benzene)ruthenium)
Ru[(R, R)-N-Tf-1,2-cyclohexanediamine](η⁶-benzene)(((R, R)-N-trifluoromethanesulfonyl-1,2-cyclohexanediamine) (η⁶-benzene)ruthenium)
Ru[(S, S)-N-Tf-1,2-cyclohexanediamine] (η⁶-p-cymene) (((S, S)-N-trifluoromethanesulfonyl-1,2-cyclohexanediamine)(η⁶-p-cymene)ruthenium)
Ru[(R, R)-N-Tf-1,2-cyclohexanediamine] (η⁶-p-cymene) (((R, R)-N-trifluoromethanesulfonyl-1,2-cyclohexanediamine)(η⁶-p-cymene)ruthenium)
Ru[(S, S)-N-Tf-1,2-cyclohexanediamine](η⁶-mesitylene) (((S, S)-N-trifluoromethanesulfonyl-1,2-cyclohexanediamine)(η⁶-mesitylene)ruthenium)
Ru[(R, R)-N-Tf-1,2-cyclohexanediamine](η⁶-mesitylene) (((R, R)-N-trifluoromethanesulfonyl-1,2-cyclohexanediamine)(η⁶-mesitylene)ruthenium)
Ru[(S, S)-N-C₄H₅SO₂-1,2-cyclohexanediamine](η⁶-benzene)(((S, S)-N-benzenesulfonyl-1,2-cyclohexanediamine)(η⁶-benzene)ruthenium)
Ru[(R, R)-N-C₆H₅SO₂-1,2-cyclohexanediamine](η²-benzene) (((R, R)-N-benzenesulfonyl-1,2-cyclohexanediamine)(η⁶-benzene)ruthenium)
Ru[(S, S)-N-C₆H₅SO₂-1,2-cyclohexanediamine](η⁶-p-cymene) (((S, S)-N-benzenesulfonyl-1,2-cyclohexanediamine) (η⁶-p-cymene)ruthenium)
Ru[(R, R)-N-C₆H₅SO₂-1,2-cyclohexanediamine](η⁶-p-cymene) (((R, R)-N-benzenesulfonyl-1,2-cyclohexanediamine)(η⁶-p-cymene)ruthenium)
Ru[(S, S)-N-C₆H₅SO₂-1,2-cyclohexanediamine](η⁶-mesitylene)(((S, S)-N-benzenesulfonyl-1,2-cyclohexanediamine) (η⁶-mesitylene)ruthenium)
Ru[(R, R)-N-C₆H₅SO₂-1,2-cyclohexanediamine](η⁶-mesitylene)(((R, R)-N-benzenesulfonyl-1,2-cyclohexanediamine) (η⁶-mesitylene)ruthenium)

Those of the formula (VII) wherein m and n are simultaneously 1 are illustrated as follows. Herein, η is used to represent the number of carbon atoms bonded to a metal in unsaturated ligands, and therefore, hexahapto (six carbon atoms bonded to metal) is represented by η⁶; p-Ts represents p-toluenesulfonyl group; Ms represents methanesulfonyl group; and Tf represents trifluoromethanesulfonyl group.

RuH[(S, S)-p-TsNCH(C₆H₅)CH(C₆H₅)NH₂](η⁶-benzene) (hydride-((S, S)-N-p-toluenesulfonyl-1,2-diphenylethylenediamine)(η⁶-benzene)ruthenium)
RuH[(R, R)-p-TsNCH(C₆H₅)CH(C₆H₅)NH₂](η⁶-benzene) (hydride-((R, R)-N-p-toluenesulfonyl-1,2-diphenylethylenediamine)(η⁶-benzene)ruthenium)
RuH[(S, S)-p-TsNCH(C₆H₅)CH(C₆H₅)NH₂](η⁶-p-cymene) (hydride-((S, S)-N-p-toluenesulfonyl-1,2-diphenylethylenediamine)(η⁶-p-cymene)ruthenium)
RuH[(R, R)-p-TsNCH(C₆H₅)CH(C₆H₅)NH₂](η⁶-p-cymene)(hydride-((R, R)-N-p-toluenesulfonyl-1,2-diphenylethylenediamine)(η⁶-p-cymene)ruthenium)
RuH[(S, S)-p-TsNCH(C₆H₅)CH(C₆H₅)NH₂](η⁶-mesitylene) (hydride-((S, S)-N-p-toluenesulfonyl-1,2-diphenylethylenediamine)(η⁶-mesitylene)ruthenium)
RuH[(R, R)-p-TsNCH(C₆H₅)CH(C₆H₅)NH₂](η⁶-mesitylene) (hydride-((R, R)-N-p-toluenesulfonyl-1,2-diphenylethylenediamine)(η⁶-mesitylene)ruthenium)
RuH[(S, S)-MsNCH(C₆H₅)CH(C₆H₅)NH₂](η⁶-benzene) (hydride-((S, S)-N-methanesulfonyl-1,2-diphenylethylenediamine)(η⁶-benzene)ruthenium)
RuH[(R, R)-MsNCH(C₆H₅)CH(C₆H₅)NH₂](η⁶-benzene) (hydride-((R, R)-N-methanesulfonyl-1,2-diphenylethylenediamine)(η⁶-benzene)ruthenium)
RuH[(S, S)-MSNCH(C₆H₅)CH(C₆H₅)NH₂](η⁶-p-cymene) (hydride-((S, S)-N-methanesulfonyl-1,2-diphenylethylenediamine) (η⁶-p-cymene)ruthenium)
RuH[(R, R)-MsNCH(C₆H₅)CH(C₆H₅)NH₂](η⁶-p-cymene) (hydride-((R, R)-N-methanesulfonyl-1,2-diphenylethylenediamine)(η⁶-p-cymene)ruthenium)
RuH[(S, S)-MsNCH(C₆H₅)CH(C₆H₅)NH₂](η⁶-mesitylene) (hydride-((S, S)-N-methanesulfonyl-1,2-diphenylethylenediamine)(η⁶-mesitylene)ruthenium)
RUH[(R, R)-MsNCH(C₆H₅)CH(C₆H₅)NH](η⁶-mesitylene) (hydride-((R, R)-N-methanesulfonyl-1,2-diphenylethylenediamine)(η⁶-mesitylene)ruthenium)
RuH[(S, S)-TfNCH(C₆H₅)CH(C₆H₅)NH₂](η⁶-benzene) (hydride-((S, S)-N-trifluoromethanesulfonyl-1,2-diphenylethylenediamine) (η⁶-benzene)ruthenium)
RuH[(R, R)-TfNCH(C₆H₅)CH(C₆H₅)NH₂](η⁶-benzene) (hydride-((R, R)-N-trifluoromethanesulfonyl-1,2-diphenylethylenediamine) (η⁶-benzene) ruthenium)
RuH[(S, S)-TfNCH(C₆H₅)CH(C₆H₅)NH₂](η⁶-p-cymene) (hydride-((S, S)-N-trifluoromethanesulfonyl-1,2-diphenylethylenediamine) (η⁶-p-cymene)ruthenium)
RuH[(R, R)-TfNCH(C₆H₅)CH(C₆H₅)NH₂](η⁶-p-cymene) (hydride-((R, R)-N-trifluoromethanesulfonyl-1,2-diphenylethylenediamine) (η⁶-p-cymene)ruthenium)
RuH[(S, S)-TfNCH(C₆HS)CH(C₆H₅)NH₂](η⁶-mesitylene) (hydride-((S, S)-N-trifluoromethanesulfonyl-1,2-diphenylethylenediamine) (η⁶-mesitylene) ruthenium)
RuH[(R, R)-TfNCH(C₆H₅)CH(C₆H₅)NH₂](η⁶-mesitylene) (hydride-((R, R)-N-trifluoromethanesulfonyl-1,2-diphenylethylenediamine)(η⁶-mesitylene)ruthenium)
RuH[(S, S)-C₆H₅SO₂NCH(C₆H₅)CH(C₆H₅)NH₂](η⁶-benzene)(hydride-((S, S)-N-benzenesulfonyl-1,2-diphenylethylenediamine)(η⁶-benzene)ruthenium)

RuH[(R, R)-C$_6$H$_5$SO$_2$NCH(C$_6$H$_5$) CH(C$_6$H$_5$)NH$_2$]($\eta^6$-benzene) (hydride-((R, R)-N-benzenesulfonyl-1,2-diphenylethylenediamine)($\eta^6$-benzene)ruthenium)

RuH[(S, S)-C$_6$H$_5$SO$_2$NCH(C$_6$H$_5$)CH(C$_6$H$_5$)NH$_2$]($\eta^6$-p-cymene)(hydride-((S, S)-N-trifluoromethanesulfonyl-1,2-diphenylethylenediamine)($\eta^6$-p-cymene)ruthenium)

RuH[(R, R)-C$_6$H$_5$SO$_2$NCH(C$_6$H$_5$)CH(C$_6$H$_5$)NH$_2$]($\eta^6$-p-cymene)(hydride-((R, R)-N-trifluoromethanesulfonyl-1,2-diphenylethylenediamine) ($\eta^6$-p-cymene)ruthenium)

RuH[(S, S)-C$_6$H$_5$SO$_2$NCH(C$_6$H$_5$)CH(C$_6$H$_5$)NH$_2$]($\eta^6$-mesitylene)(hydride-((S, S)-N-benzenesulfonyl-1,2-diphenylethylenediamine) ($\eta^6$-mesitylene)ruthenium)

RuH[(R, R)-C$_6$H$_5$SO$_2$NCH(C$_6$H$_5$)CH(C$_6$H$_5$)NH$_2$]($\eta^6$-mesitylene)(hydride-((R, R)-N-benzenesulfonyl-1,2-diphenylethylenediamine)($\eta^6$-mesitylene)ruthenium)

RuH[(S, S)-N-p-Ts-1,2-cyclohexanediamine]($\eta^6$-benzene) (hydride-((S, S)-N-p-toluenesulfonyl-1,2-cyclohexanediamine)($\eta^6$-benzene)ruthenium)

RuH[(R, R)-N-p-Ts-1,2-cyclohexanediamine]($\eta^6$-benzene) (hydride-((R, R)-N-p-toluenesulfonyl-1,2-cyclohexanediamine)($\eta^6$-benzene)ruthenium)

RuH[(S, S)-N-p-Ts-1,2-cyclohexanediamine]($\eta^6$-p-cymene) (hydride-((S, S)-N-p-toluenesulfonyl-1,2-cyclohexanediamine)($\eta^6$-p-cymene)ruthenium)

RuH[(R, R)-N-p-Ts-1,2-cyclohexanediamine]($\eta^6$-p-cymene)(hydride-((R, R)-N-p-toluenesulfonyl-1,2-cyclohexanediamine)($\eta^6$-p-cymene)ruthenium)

RuH[(S, S)-N-p-Ts-1,2-cyclohexanediamine]($\eta^6$-mesitylene)(hydride-((S, S)-N-p-toluenesulfonyl-1,2-cyclohexanediamine)($\eta^6$-mesitylene)ruthenium)

RuH[(R, R)-N-p-Ts-1,2-cyclohexanediamine]($\eta^6$-mesitylene) (hydride-((R, R)-N-p-toluenesulfonyl-1,2-cyclohexanediamine)($\eta^6$-mesitylene)ruthenium)

RuH[(S, S)-N-Ms-1,2-cyclohexanediamine]($\eta^6$-benzene) (hydride-((S, S)-N-methanesulfonyl-1,2-cyclohexanediamine) ($\eta^6$-benzene)ruthenium)

RuH[(R, R)-N-Ms-1,2-cyclohexanediamine]($\eta^6$-benzene) (hydride-((R, R)-N-methanesulfonyl-1,2-cyclohexanediamine) ($\eta^6$-benzene)ruthenium)

RuH[(S, S)-N-Ms-1,2-cyclohexanediamine]($\eta^6$-p-cymene) (hydride-((S, S)-N-methanesulfonyl-1,2cyclohexanediamine) ($\eta_6$-p-cymene)ruthenium)

RuH[(R, R)-N-Ms-1,2-cyclohexanediamine]($\eta^6$-p-cymene) (hydride-((R, R)-N-methanesulfonyl-1,2-cyclohexanediamine) ($\eta^6$-p-cymene)ruthenium)

RuH[(S, S)-N-Ms-1,2-cyclohexanediamine]($\eta^6$-mesitylene) (hydride-((S, S)-N-methanesulfonyl-1,2-cyclohexanediamine) ($\eta^6$-mesitylene) ruthenium)

RuH[(R, R)-N-MS-1,2-cyclohexanediamine]($\eta^6$-mesitylene) (hydride-((R, R)-N-methanesulfonyl-1,2-cyclohexanediamine)($\eta^6$-mesitylene)ruthenium)

RuH[(S, S)-N-Tf-1,2-cyclohexanediamine]($\eta_6$-benzene) (hydride-((S, S)-N-trifluoromethanesulfonyl-1,2-cyclohexanediamine)($\eta^6$-benzene)ruthenium)

RuH[(R, R)-N-Tf-1,2-cyclohexanediamine]($\eta^6$-benzene) (hydride-((R, R)-N-trifluoromethanesulfonyl-1,2-cyclohexanediamine) ($\eta^6$-benzene)ruthenium)

RuH[(S, S)-N-Tf-1,2-cyclohexanediamine]($\eta^6$-p-cymene) (hydride-((S, S)-N-trifluoromethanesulfonyl-1,2-cyclohexanediamine)($\eta^6$-p-cymene)ruthenium)

RuH[(R, R)-N-Tf-1,2-cyclohexanediamine]($\eta^6$-p-cymene) (hydride-((R, R)-N-trifluoromethanesulfonyl-1,2-cyclohexanediamine)($\eta^6$-p-cymene) ruthenium)

RuH[(S, S)-N-Tf-1,2-cyclohexanediamine]($\eta^6$-mesitylene) (hydride-((S, S)-N-trifluoromethanesulfonyl-1,2-cyclohexanediamine)($\eta^6$-mesitylene)ruthenium)

RuH[(R, R)-N-Tf-1,2-cyclohexanediamine]($\eta^6$-mesitylene) (hydride-((R, R)-N-trifluoromethanesulfonyl-1,2-cyclohexanediamine)($\eta^6$-mesitylene)ruthenium)

RuH[(S, S)-N-C$_6$H$_5$SO$_2$-1,2-cyclohexanediamine]($\eta^6$-benzene)(hydride-((S, S)-N-benzenesulfonyl-1,2-cyclohexanediamine)($\eta^6$-benzene) ruthenium)

RuH[(R, R)-N-C$_6$H$_5$SO$_2$-1,2-cyclohexanediamine]($\eta^6$-benzene) (hydride-((R, R)-N-benzenesulfonyl-1,2-cyclohexanediamine)($\eta^6$-benzene)ruthenium)

RuH[(S, S)-N-C$_6$H$_5$SO$_2$-1,2-cyclohexanediamine]($\eta^6$-p-cymene)(hydride-((S, S)-N-benzenesulfonyl-1,2-cyclohexanediamine)($\eta^6$-p-cymene) ruthenium)

RuH[(R, R)-N-C$_6$H$_5$SO$_2$-1,2-cyclohexanediamine]($\eta^6$-p-cymene)(hydride-((R, R)-N-benzeneesulfonyl-1,2-cyclohexanediamine)($\eta^6$-p-cymene)ruthenium)

RuH[(S, S)-N-C$_6$H$_5$SO$_2$-1,2-cyclohexanediamine]($\eta^6$-mesitylene)(hydride-((S, S)-N-benzenesulfonyl-1,2-cyclohexanediamine) ($\eta^6$-mesitylene)ruthenium)

RuH[(R, R)-N-C$_6$H$_5$SO$_2$-1,2-cyclohexanediamine]($\eta^6$-mesitylene)(hydride-((R, R)-N-benzenesulfonyl-1,2-cyclohexanediamine) ($\eta^6$-mesitylene)ruthenium)

Among the compounds represented by the general formula (VII) in accordance with the present invention, the complex of the formula (VII) wherein m and n are simultaneously 0 can be produced as follows. More specifically, Ru[(S, S)-, (R, R)-TsNCH(R$^{01}$)CH(R$^{02}$) NH[($\eta^6$-p-cymene) (((S, S) and (R, R)-N-toluenesulfonyl-1,2-disubstituted ethylenediamine)($\eta^6$-p-cymene)ruthenium (wherein R$^{01}$ and R$^{02}$ are the same as described above and Ts is p-toluenesulfonyl group), is readily synthesized by reacting a raw material [RuCl$_2$($\eta^6$-p-cymene)$_2$(tetrachlorobis($\eta^6$-p-cymene)diruthenium) prepared by the method described in a reference J. Chem. Soc., Dalton Trans., pp.233–241(1974) with (S, S)-, (R, R)-TSNHCH(R$^{01}$)CH(R$^{02}$)NH$_2$((S, S) and (R, R)-N-p-toluenesulfonyl-1,2-disubstituted ethylenediamine) in the presence of alkali metal hydroxide or alkali metal alcolate in a solvent.

The reaction is generally carried out quantitatively, by reacting a raw material [RuCl$_2$($\eta^6$-p-cymene)]$_2$ (tetrachlorobis($\eta^6$-p-cymene)diruthenium (1 mole) and (S, S)-, (R, R)-TsNHCH(R$^{01}$)CH(R$^{02}$)NH,(((S, S) and (R, R)-N-p-toluenesulfonyl-1,2-disubstituted ethylenediamine)(2 moles) with alkali metal hydroxide or alkali metal alcolate in the stream of inactive gases such nitrogen, helium or argon in an inactive solvent at a temperature of –10 to 50° C. for 30 minutes to 3 hours, and leaving the reaction product to stand alone, prior to liquid separation procedure to remove the aqueous phase, and subsequently removing the solvent under reduced pressure.

The alkali metal hydroxide or alkali metal alcolate specifically includes NaOH, NaOCH$_3$, NaOC$_2$H$_5$, KOH, KOCH$_3$, KOC$_2$H$_5$, LiOH, LiOCH$_3$, and LiOC$_2$H$_5$, preferably including NaOH or KOH. The amount of the alkali metal hydroxide or alkali metal alcolate is 5 to 10 fold the amount of ruthenium. The inactive solvent appropriately includes for example hydrocarbons such as benzene, toluene, xylene, cyclohexane, and methylcyclohexane; ethers such as dimethyl ether, diethyl ether, diisopropyl ether, methyl-tert-butyl ether, tetrahydrofuran, 1,3-dioxolanee, and 1,4-dioxane; halogenated hydrocarbons such as chloroform, methylene chloride and chlorobenzene.

The complex can be produced by another method. Specifically, Ru[(S, S)-, (R, R)-TsNCH(R$^{01}$)CH(R$^{02}$)NH] ($\eta^6$-p-cymene)(((S, S) and (R, R)-N-toluenesulfonyl-1,2-disubstituted ethylenediamine)($\eta^6$-p-cymene)ruthenium (wherein R$^{01}$ and R$^{02}$ are the same as described above and Ts is p-toluenesulfonyl group), is readily synthesized by reacting a raw material RuCl[(S, S)-, (R, R)- TsNCH(R$^{01}$) CH(R$^{02}$)NH$_2$]($\eta^6$-p-cymene)(chloro-((S, S) and (R, R)-N-p-toluenesulfonyl-1,2-disubstituted ethylenediamine)($\eta^6$-p- cymene)ruthenium prepared through the reaction of [RUCl$_2$ ($\eta^6$-p-cymene) $_2$(tetrachlorobis($\eta^6$-p-cymene)diruthenium, (S, S)-, (R, R)-TsNHCH(R$^{O1}$)CH(R$^{O2}$)NH$_2$((S, S) and (R, R)-N-p-toluenesulfonyl-1,2-disubstituted ethylenediamine) with a tertiary amine (for example, triethylamine) for example by the method described in J. Am. Chem. Soc., Vol.117, pp.7562–7563 (1995), J. Am. Chem. Soc., Vol.118, pp.2521–2522 (1996) and J. Am. Chem. Soc., Vol.118, pp.4916–4917 (1996), in the presence of alkali metal hydroxide or alkali metal alcolate in a solvent.

The reaction is generally carried out quantitatively, by reacting a raw material RUCl[(S, S)-, (R, R)-TsNCH(R$^{O1}$) CH(R$^{O2}$)NH$_2$]($\eta^6$-p-cymene)(chloro-((S, S) and (R, R)-N-p-toluenesulfonyl-1,2-disubstituted ethylenediamine) ($\eta^6$-p-cymene)ruthenium) (1 mole) with alkali metal hydroxide or alkali metal alcolate in the stream of inactive gases such nitrogen, helium or argon in an inactive solvent at a temperature of −10 to 50° C. for 30 minutes to 3 hours, and leaving the reaction product to stand alone, prior to liquid separation procedure to remove the aqueous phase, and subsequently removing the solvent under reduced pressure.

The alkali metal hydroxide or alkali metal alcolate specifically includes NaOH, NaOCH$_3$, NAOC$_2$H$_5$, KOH, KOCH$_3$, KOC$_2$H$_5$, LiOH, LiOCH$_3$, and LiOC$_2$H$_5$, preferably including NaOH or KOH. The amount of the alkali metal hydroxide or alkali metal alcolate is 1 to 2-fold in mole the amount of ruthenium. The inactive solvent appropriately includes for example hydrocarbons such as benzene, toluene, xylene, cyclohexane, and methylcyclohexane; ethers such as dimethyl ether, diethyl ether, diisopropyl ether, methyltert-butyl ether, tetrahydrofuran, 1,3-dioxolane, and 1,4,-dioxane; and halogenated hydrocarbons such as chloroform, methylene chloride and chlorobenzene.

In accordance with the present invention, the complex represented by the general formula (V) wherein m and n are simultaneously 1 can be produced as follows. More specifically, RuH[(S, S)-, (R, R)-TsNCH(R$^{O1}$)CH(R$^{O2}$)NH$_2$] ($\eta^6$-p-cymene)(hydride-((S, S) and (R, R)-N-toluenesulfonyl-1,2-disubstituted ethylenediamine) ($\eta^6$-p-cymene)ruthenium) (wherein R$^{O1}$ and R$^{O2}$ are the same as described above and Ts is p-toluenesulfonyl group), is readily synthesized, by reacting a raw material Ru[(S, S)-, (R, R)-TSNCH(R$^{O1}$)CH(R$^{O2}$)NH] ($\eta^6$-p-cymene)(((S, S) and (R, R)-N-toluenesulfonyl-1,2-disubstituted ethylenediamine) ($\eta^6$-p-cymene) ruthenium)(wherein R$^{O1}$ and R$^{O2}$ are the same as defined above; and Ts represents p-toluenesulfonyl group) in an alcohol solvent.

The reaction is generally carried out quantitatively, by reacting a raw material Ru[(S, S)-, (R, R)-TsNCH(R$^{O1}$)CH (R$^{O2}$)NH] ($\eta^6$-p-cymene)(((S, S) and (R, R)-N-toluenesulfonyl-1,2-disubstituted ethylenediamine) ($\eta^6$-p-cymene)ruthenium) (wherein R$^{O1}$ and R$^{O2}$ are the same as defined above; and Ts represents p-toluenesulfonyl group) in an inactive gas stream in an alcohol solvent at a temperature of 0 to 100° C. for 3 minutes to 1 hour for hydrogen transfer reaction, and subsequently removing the solvent under reduced pressure. Appropriate alcohol solvents include for example methanol, ethanol, n-propanol, isopropanol, n-butanol, iso-butanol, and sec-butanol.

The complex can be produced by another method. Specifically, RuH[(S, S)-, (R, R)-TSNCH(R$^{O1}$)CH(R$^{O2}$) NH$_2$]($\eta^6$-p-cymene)(hydride-((S, S) and (R, R)-N-p-toluenesulfonyl-1,2-disubstituted ethylenediamine) ($\eta^6$-p-cymene)ruthenium) (wherein R$^{O1}$ and R$^{O2}$ are the same as described above and Ts is p-toluenesulfonyl group), is readily synthesized, by reacting for example a raw material Ru[(S, S)-, (R, R)-TsNCH(R$^{O1}$)CH(R$^{O2}$)NH] ($\eta^6$-p-cymene) (((S, S) and (R, R)-N-toluenesulfonyl-1,2-disubstituted ethylenediamine) ($\eta^6$-p-cymene) ruthenium) (wherein R$^{O1}$ and R$^{O2}$ are the same as defined above; and Ts represents p-toluenesulfonyl group), in a solvent in pressurized hydrogen.

The reaction is generally carried out quantitatively, by hydrogenating a raw material RuH[(S, S)-, (R, R)-TsNCH (R$^{O1}$)CH(R$^{O2}$)NH$_2$ ($\eta^6$-p-cymene)(hydride-((S, S) and (R, R)-N-toluenesulfonyl-1,2-disubstituted ethylenediamine) ($\eta^6$-p-cymene)ruthenium)(wherein R$^{O1}$ and R$^{O2}$ are the same as defined above; and Ts represents p-toluenesulfonyl group), in an inactive solvent at a temperature of 0 to 50° C. for 30 minutes to 24 hours (preferably 1 to 10 hours) in pressurized hydrogen and subsequently removing the solvent under reduced pressure. The hydrogen pressure is within a range of 1 to 150 atm, preferably 20 to 100 atm.

Appropriate inactive solvents include for example hydrocarbons such as benzene, toluene, xylene, hexane, heptane, cyclohexane, and methylcyclohexane; and ethers such as dimethyl ether, diethyl ether, diisopropyl ether, methyl-tert-butyl ether, tetrahydrofuran, 1,3-dioxolane and 1,4-dioxane.

An optically active diamine of the formula (S, S)-, (R, R)-R$^{O3}$NHCH(R$^{O1}$)CH(R$^{O2}$)NH$_2$((S, S) and (R, R)-N-substituted-1,2-disubstituted ethylenediamines) (wherein R$^{O1}$ R$^{O2}$ and R$^{O3}$ are the same as described above) is synthesized, by using raw materials (S, S)-, (R, R)-NH$_2$CH (R$^{O1}$)CH(R$^{O2}$)NH$_2$((S, S) and (R, R)-1,2-disubstituted ethylenediamines in a conventional manner [Protective Groups in Organic Synthesis, Vol.2, pp.309–405(1991)]. More specifically, (S, S)-, (R, R)-TsNHCH(R$^{O1}$)CH(R$^{O2}$)NH$_2$((S, S) and (R, R)-N-P-toluenesulfonyl-1,2-disubstituted ethylenediamines) (wherein R$^{O1}$ and R$^{O2}$ are the same as defined above; and Ts represents p-toluenesulfonyl group) are readily synthesized, by reacting for example (S, S)-, (R, R)-NH$_2$CH(R$^{O1}$)CH(R$^{O2}$)NH$_2$((S, S) and (R, R)-1,2-disubstituted ethylenediamines) as raw materials with TsCl (p-toluenesulfonyl chloride) in the presence of an alkali (for example, tertiary amine, alkali metal salts and the like) in a solvent.

The reaction is generally carried out quantitatively, by reacting together (S, S)-, (R, R)-NH$_2$CH(R$^{O1}$)CH(R$^{O2}$)NH$_2$ ((S, S) and (R, R)-1,2-disubstituted ethylenediamines) (1 mole) and TsCl (p-toluenesulfonyl chloride) (1 mole) with an alkali (for example, triethylamine) in an inactive solvent (for example, toluene, tetrahydrofuran, and methylene chloride) in an inactive gas stream such as nitrogen, helium or argon or the like at a temperature of 0 to 50° C. for 30 minutes to 3 hours, subsequently adding water to the resulting mixture to gently leave the reaction product to stand, prior to liquid separation procedure, to remove the aqueous phase, and evaporating the solvent under reduced pressure.

The optically active diamine (S, S)-, (R, R)—NH$_2$CH (R$^{O1}$)CH(R$^{O2}$)NH$_2$((S, S) and (R, R)-1,2-disubstituted ethylenediamines)(wherein R$^{O1}$ and R$^{O2}$ are the same as defined above), is known and is sometimes commercially available or can be produced in a conventional manner or by conventional resolution process of racemates (Tetrahedron Lett., Vol.32, pp.999–1002) (1991), Tetrahedron Lett., Vol.34, pp.1905–1908 (1993)].

(S, S) and (R, R)-1,2-diphenylethylenediamines and (S, S) and (R, R)-1,2-cyclohexanediamines are commercially available.

For example, the optically active diamine of the general formula (e) can be produced by the following method (Tetrahedron Lett., Vol.32, pp.999–1002 (1991)].

The optically active diamine of the general formula (e) ((S, S) and (R, R)-1,2-disubstituted ethylenediamines) can be produced readily at a high yield, by preparing cyclophosphate from raw materials optically active 1,2-disubstituted ethylene diols, which is then reacted with amidine to recover imidazoline, and ring opening the imidazoline by using an acid catalyst.

The ruthenium-diamine complex of the present invention may be isolated and used, but while generating the complex in a reaction solution, the resulting complex is used as a catalyst for asymmetric synthesis and the like.

The method for producing optically active secondary alcohols by utilizing the complex of the present invention as a hydrogen transfer-type oxidation catalyst will now be described below.

The racemic secondary alcohols or meso-type diols to be used as the reaction substrates for producing optically active secondary alcohols are represented by the aforementioned formulas (VIII) and (IXI). In the formula (VIII), the racemic secondary alcohols in this case specifically include 1-phenylethanol, 1-(2-methylphenyl)ethanol, 1-(2-ethylphenyl)ethanol, 1-(2-isopropylphenyl)ethanol, 1-(2-tert-butylphenyl)ethanol, 1-(2-methoxyphenyl)ethanol, 1-(2-ethoxyphenyl)ethanol, 1-(2-isopropoxyphenyl)ethanol, 1-(2-tert-butoxyphenyl)ethanol, 1-(2-dimethylaminophenyl)ethanol, 1-(3-methylphenyl)ethanol, 1-(3-ethylphenyl)ethanol, 1-(3-isopropylphenyl)ethanol, 1-(3-tert-butylphenyl)ethanol, 1-(3-methoxyphenyl)ethanol, 1-(3-ethoxyphenyl)ethanol, 1-(3-isopropoxyphenyl)ethanol, 1-(3-tert-butoxyphenyl)ethanol, 1-(3-dimethylaminophenyl)ethanol, 1-(4-methylphenyl)ethanol, 1-(4-ethylphenyl)ethanol, 1-(4-isopropylphenyl)ethanol, 1-(4-tert-butylphenyl)ethanol, 1-(4-methoxyphenyl)ethanol, 1-(4-ethoxyphenyl)ethanol, 1-(4-isopropoxyphenyl)ethanol, 1-(4-tert-butoxyphenyl)ethanol, 1-(4-dimethylaminophenyl)ethanol, 1-cumenylethanol, 1-mesitylethanol, 1-xylylethanol, 1-(1-naphthyl)ethanol, 1-(2-naphthyl)ethanol, 1-phenanthrylethanol, 1-indenylethanol, 1-(3,4-dimethoxyphenyl)ethanol, 1-(3,4-diethoxyphenyl)ethanol, 1-(3,4-methylenedioxyphenyl)ethanol, 1-ferrocenylethanol, 1-phenylpropanol, 1-(2-methylphenyl)propanol, 1-(2-ethylphenyl)propanol, 1-(2-isopropylphenyl)propanol, 1-(2-tert-butylphenyl)propanol, 1-(2-methoxyphenyl)propanol, 1-(2-ethoxyphenyl)propanol, 1-(2-isopropoxyphenyl)propanol, 1-(2-tert-butoxyphenyl)propanol, 1-(2-dimethylaminophenyl)propanol, 1-(3-methylphenyl)propanol, 1-(3-ethylphenyl)propanol, 1-(3-isopropylphenyl)propanol, 1-(3-tert-butylphenyl)propanol, 1-(3-methoxyphenyl)propanol, 1-(3-ethoxyphenyl)propanol, 1-(3-isopropoxyphenyl)propanol, 1-(3-tert-butoxyphenyl)propanol, 1-(3-dimethylaminophenyl)propanol, 1-(4-methylphenyl)propanol, 1-(4-ethylphenyl)propanol, 1-(4-isopropylphenyl)propanol, 1-(4-tert-butylphenyl)propanol, 1-(4-methoxyphenyl)propanol, 1-(4-ethoxyphenyl)propanol, 1-(4-isopropoxyphenyl)propanol, 1-(4-tert-butoxyphenyl)propanol, 1-(4-dimethylaminophenyl)propanol, 1-cumenylpropanol, 1-mesitylpropanol, 1-xylylpropanol, 1-(1-naphthyl) propanol, 1-(2-naphthyl)propanol, 1-phenanthrylpropanol, 1-indenylpropanol, 1-(3,4-dimethoxyphenyl) propanol, 1-(3,4-diethoxyphenyl) propanol, 1-(3,4-methylenedioxyphenyl) propanol, 1-ferrocenylpropanol, 1-phenylbutanol, 1-(2-methylphenyl)butanol, 1-(2-ethylphenyl)butanol, 1-(2-isopropylphenyl)butanol, 1-(2-tert-butylphenyl)butanol, 1-(2-methoxyphenyl)butanol, 1-(2-ethoxyphenyl)butanol, 1-(2-isopropoxyphenyl)butanol, 1-(2-tert-butoxyphenyl)butanol, 1-(2-dimethylaminophenyl)butanol, 1-(3-methylphenyl)butanol, 1-(3-ethylphenyl)butanol, 1-(3-isopropylphenyl)butanol, 1-(3-tert-butylphenyl)butanol, 1-(3-methoxyphenyl)butanol, 1-(3-ethoxyphenyl)butanol, 1-(3-isopropoxyphenyl)butanol, 1-(3-tert-butoxyphenyl)butanol, 1-(3-dimethylaminophenyl)butanol, 1-(4-methylphenyl)butanol, 1-(4-ethylphenyl)butanol, 1-(4-isopropylphenyl)butanol, 1-(4-tert-butylphenyl)butanol, 1-(4-methoxyphenyl)butanol, 1-(4-ethoxyphenyl)butanol, 1-(4-isopropoxyphenyl)butanol, 1-(4-tert-butoxyphenyl)butanol, 1-(4-dimethylaminophenyl)butanol, 1-cumenylbutanol, 1-mesitylbutanol, 1-xylylbutanol, 1-(1-naphthyl)butanol, 1-(2-naphthyl)butanol, 1-phenanthrylbutanol, 1-indenylbutanol, 1-(3,4-dimethoxyphenyl)butanol, 1-(3,4-diethoxyphenyl)butanol, 1-(3,4-methylenedioxyphenyl)butanol, 1-ferrocenylbutanol, 1-phenylisobutanol, 1-(2-methylphenyl)isobutanol, 1-(2-ethylphenyl)isobutanol, 1-(2-isopropylphenyl)isobutanol, 1-(2-tert-butylphenyl)isobutanol, 1-(2-methoxyphenyl)isobutanol, 1-(2-ethoxyphenyl)isobutanol, 1-(2-isopropoxyphenyl)isobutanol, 1-(2-tert-butoxyphenyl)isobutanol, 1-(2-dimethylaminophenyl)isobutanol, 1-(3-methylphenyl)isobutanol, 1-(3-ethylphenyl)isobutanol, 1-(3-isopropylphenyl)isobutanol, 1-(3-tert-butylphenyl)isobutanol, 1-(3-methoxyphenyl)isobutanol, 1-(3-ethoxyphenyl)isobutanol, 1-(3-isopropoxyphenyl)isobutanol, 1-(3-tert-butoxyphenyl)isobutanol, 1-(3-dimethylaminophenyl)isobutanol, 1-(4-methylphenyl)isobutanol, 1-(4-ethylphenyl)isobutanol, 1-(4-isopropylphenyl)isobutanol, 1-(4-tert-butylphenyl)isobutanol, 1-(4-methoxyphenyl)isobutanol, 1-(4-ethoxyphenyl)isobutanol, 1-(4-isopropoxyphenyl)isobutanol, 1-(4-tert-butoxyphenyl)isobutanol, 1-(4-dimethylaminophenyl)isobutanol, 1-cumenylisobutanol, 1-mesitylisobutanol, 1-xylylisobutanol, 1-(1-naphthyl)isobutanol, 1-(2-naphthyl)isobutanol, 1-phenanthrylisobutanol, 1-indenylisobutanol, 1-(3,4-dimethoxyphenyl)isobutanol, 1-(3,4-diethoxyphenyl)isobutanol, 1-(3,4-methylenedioxyphenyl)isobutanol, 1-ferrocenylisobutanol, 1-phenylpentanol, 1-(2-methylphenyl)pentanol, 1-(2-ethylphenyl)pentanol, 1-(2-isopropylphenyl)pentanol, 1-(2-tert-butylphenyl)pentanol, 1-(2-methoxyphenyl)pentanol, 1-(2-ethoxyphenyl)pentanol, 1-(2-isopropoxyphenyl)pentanol, 1-(2-tert-butoxyphenyl) pentanol, 1-(2-dimethylaminophenyl)pentanol, 1-(3-methylphenyl)pentanol, 1-(3-ethylphenyl)pentanol, 1-(3-isopropylphenyl)pentanol, 1-(3-tert-butylphenyl)pentanol, 1-(3-methoxyphenyl)pentanol, 1-(3-ethoxyphenyl)pentanol, 1-(3-isopropoxyphenyl)pentanol, 1-(3-tert-butoxyphenyl) pentanol, 1-(3-dimethylaminophenyl)pentanol, 1-(4-methylphenyl)pentanol, 1-(4-ethylphenyl)pentanol, 1-(4-isopropylphenyl)pentanol, 1-(4-tert-butylphenyl)pentanol, 1-(4-methoxyphenyl)pentanol, 1-(4-ethoxyphenyl)pentanol, 1-(4-isopropoxyphenyl)pentanol, 1-(4-tert-butoxyphenyl) pentanol, 1-(4-dimethylaminophenyl)pentanol, 1-cumenylpentanol, 1-mesitylpentanol, 1-xylylpentanol, 1-(1-naphthyl)pentanol, 1-(2-naphthyl)pentanol, 1-phenanthrylpentanol, 1-indenylpentanol, 1-(3,4-dimethoxyphenyl)pentanol, 1-(3,4-diethoxyphenyl) pentanol, 1-(3,4-methylenedioxyphenyl)pentanol, 1-ferrocenylpentanol, 1-indanol, 1, 2, 3, 4-tetrahydro-1-naphthol, 2-cyclopenten-1-ol, 3-methyl-2-cyclopenten-1-ol, 2-cyclohexen-1-ol, 3-methyl-2-cyclohexen-1-ol, 2-cyclohepten-1-ol, 3-methyl-2-cyclohepten-1-ol, 2-cycloocten-1-ol, 3-methyl-2-cycloocten-1-ol, and 4-hydroxy-2-cyclopenten-1-one. Additionally, the meso-type diol represented by the formula (IX) specifically represents meso-2-cyclopenten-1,4-diol, meso-2-cyclohexane-1,4-diol, meso-2-cycloheptane-1,4-diol, meso-2-cyclooctan-1,4-diol, 5,8-dihyroxy-1,4,4a, 5, 8, 8a-hexahydro-endo-1,4-methanonaphtharene and the like.

As the ruthenium-diamine complex to be used for the hydrogen transfer-type oxidation of the present invention, the optically active ligand diamine of the general formula (VII), namely (R, R) form or (S, S) form, may satisfactorily be used. Depending on the selection, an objective compound of the desired absolute configuration can be produced. Such ruthenium-diamine complex can be used at 1/10,000 to 1/10 fold in mole, preferably 1/2,000 to 1/200 fold in mole to the substrate compound.

For carrying out the reaction, the substrate compound and the ruthenium-diamine complex are added to ketone alone or an appropriate mixture of ketone with an inactive solvent, to prepare a homogenous solution, for reaction at a reaction temperature of 0 to 100° C., preferably 10 to 50° C., for 1 to 100 hours, preferably 3 to 50 hours.

Ketones including for example acetone, ketone, diethyl ketone, diisopropyl ketone, methyltert-butyl ketone, cyclopentanone, and cyclohexanone are used. More preferably, acetone is better. These ketones may satisfactorily be used singly or in a mixture with an inactive solvent. Ketones can be used at an amount of 0.1 to 30 fold (volume/weight), depending on the type of the substrate, but preferably at an amount of 2,to 5 fold (volume/weight).

Appropriate inactive solvents include for example hydrocarbons such as benzene, toluene, xylene, hexane, heptane, cyclohexane, and methylcyclohexane; and ethers such as dimethyl ether, diethyl ether, diisopropyl ether, methyltert-butyl ether, tetrahydrofuran, 1,3-dioxolane, and 1,4-dioxane.

In accordance with the present invention, the reaction may be carried out in a batchwise manner or a continuous manner.

The resulting product can be purified by known processes such as silica gel column chromatography.

EXAMPLES

Example A

Production of Optically Active Alcohols

Production examples of optically active alcohols are shown below, and the inventive method will further be described in detail. Tables 1, 2 and 3 collectively show reaction substrates, transition metal complexes and optically active amine compounds as chiral ligands, which are to be used as typical examples.

The instrumental analysis was done by using the following individual systems.

NMR: JEOL GSX-400/Varian Gemini-200 ($^1$H-NMR sample: TMS, $^{31}$P-NMR standard sample phosphoric acid)
GLC: SHIMADZU GC-17A(column: chiral CP-Cyclodextrin-b-236-M19)
HPLC: JASCO GULLIVER (column: CHIRALCEL OJ, OB-H, OB, OD)

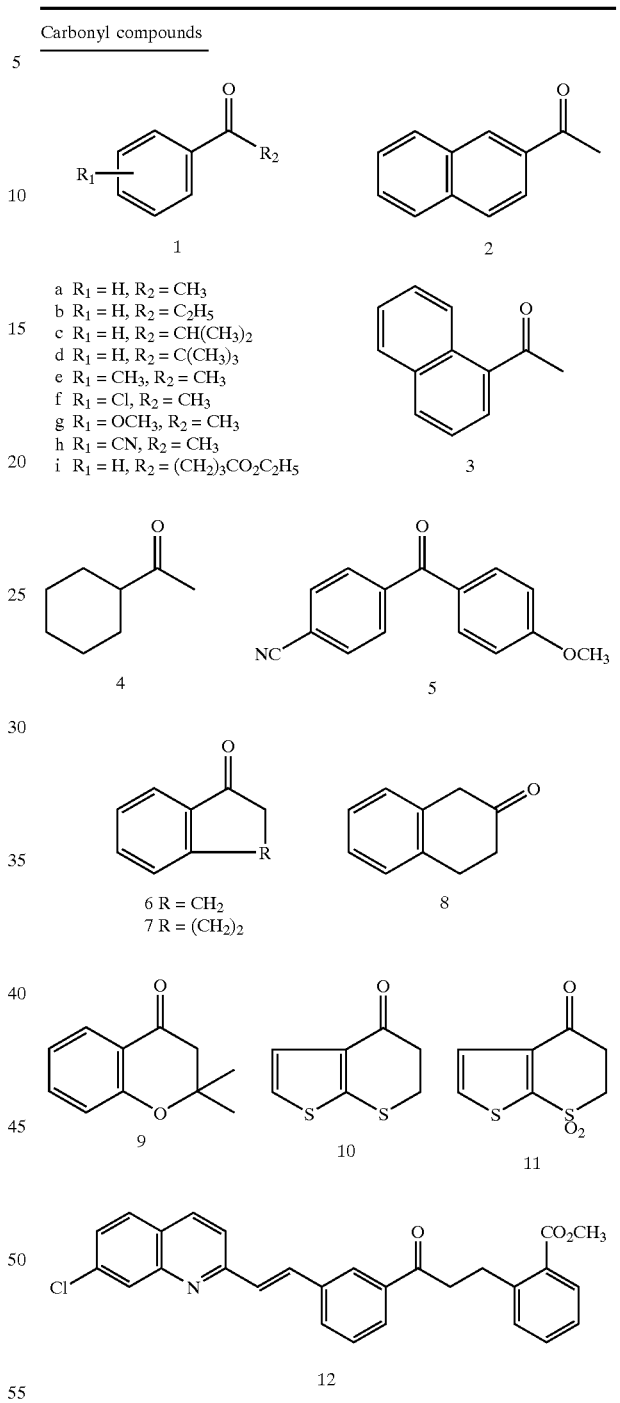

TABLE 2-continued

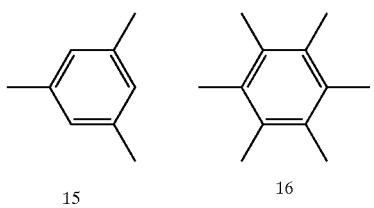

Asymmetric metal complexes

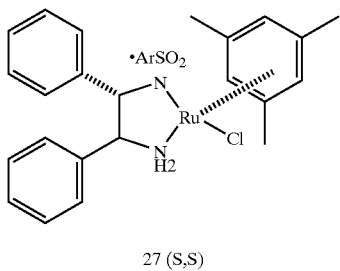

27 (S,S)

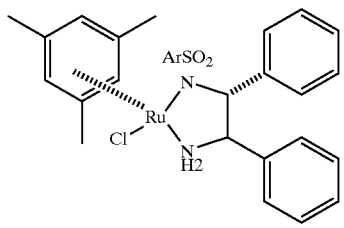

28 (R,R)

TABLE 3

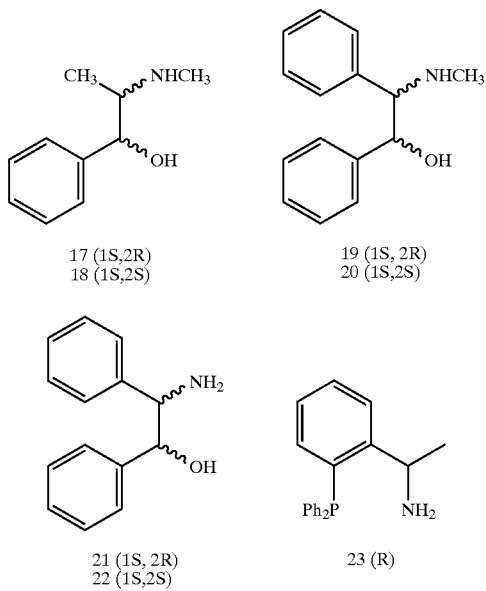

17 (1S,2R)
18 (1S,2S)

19 (1S, 2R)
20 (1S,2S)

21 (1S, 2R)
22 (1S,2S)

23 (R)

TABLE 3-continued

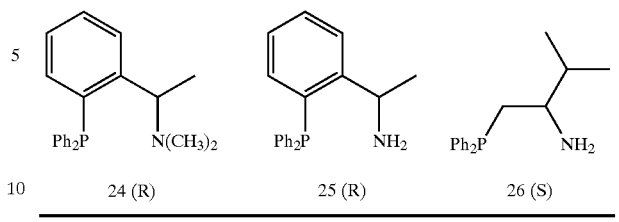

24 (R)

25 (R)

26 (S)

Examples 1 through 19

To dry 2-propanol (5.0 ml) were added various amino alcohol compounds (0.05 mmol) as chiral ligands of optically active amine compounds as shown in Table 3 and the ruthenium arene complex (0.0125 mmol) shown in Table 2, for agitation in argon or nitrogen gas atmosphere at 80° C. for 20 minutes, and the resulting mixture was cooled to room temperature, to which were then added frozen and degassed dry 2-propanol (45.0 ml), various carbonyl compounds (5 mmol) deaerated and distilled as shown in Table 1, and a solution of 0.05M KOH in 2-propanol (2.5 ml; 0.125 mmol) in this order, for subsequent agitation at room temperature. After completion of the reaction, dilute hydrochloric acid was added to adjust the resulting mixture to acidity, from which most of 2-propanol was evaporated off under reduced pressure, followed by addition of saturated sodium chloride solution. The resulting product was extracted into ethyl acetate, rinsed with saturated sodium chloride solution several times and dried over anhydrous sodium sulfate. The solvent was distilled off from the product. The final product was analyzed by $^1$H-NMR (CDC$_3$), to calculate the conversion. Then, the product was purified by thin-layer silica gel chromatography, and the isolated alcohol fraction was used to determine the optical purity and absolute configuration by HPLC or GLC. The results are collectively shown in Table 4. Furthermore, the conversion and optical purity of the sampled reaction solution can be calculated simultaneously by GLC.

Examples 20 to 23

Using the same method as in Example 1, aminophosphine compound was used as an optically active amine compound for the reaction. The results are collectively shown in Table 4.

TABLE 4

| Examples | [RuCl$_2$ (arene)]$_2$ | Ligands | Carbonyl compounds | Time | % conv | % ee | config. |
|---|---|---|---|---|---|---|---|
| 1 | 13 | 19 | 1a | 1 | 64 | 52 | S |
| 2 | 13 | 20 | 1a | 1 | 91 | 17 | S |
| 3 | 14 | 20 | 1a | 1 | 97 | 59 | S |
| 4 | 14 | 21 | 1a | 1 | 97 | 56 | S |
| 5 | 15 | 20 | 1a | 1 | 97 | 56 | S |
| 6 | 15 | 21 | 1a | 1 | 62 | 52 | S |
| 7 | 16 | 17 | 1a | 1 | 95 | 91 | S |
| 8 | 16 | 20 | 1a | 1 | 94 | 92 | S |
| 9 | 16 | 21 | 1a | 1 | 59 | 55 | S |
| 10 | 16 | 22 | 1a | 1 | 96 | 75 | S |
| 11 | 16 | 20 | 1b | 2 | 95 | 82 | S |
| 12 | 16 | 20 | 1c | 15 | 93 | 5 | S |
| 13 | 16 | 20 | 1d | 20 | 22 | 40 | R |
| 14 | 16 | 20 | o-1e | 6 | 96 | 83 | S |
| 15 | 16 | 18 | o-1f | 1 | 99 | 89 | S |
| 16 | 16 | 20 | p-1g | 4 | 73 | 79 | S |

TABLE 4-continued

| Examples | [RuCl₂(arene)]₂ | Ligands | Carbonyl compounds | Time | % conv | % ee | config. |
|---|---|---|---|---|---|---|---|
| 17 | 16 | 20 | 3 | 2 | 99 | 93 | S |
| 18 | 16 | 18 | 4 | 3 | 93 | 75 | S |
| 19 | 16 | 16 | 7 | 4 | 62 | 94 | S |
| 20 | 13 | 23 | 1a | 1 | 65 | 0.4 | S |
| 21 | 13 | 24 | 1a | 1 | 61 | 61 | R |
| 22 | 13 | 25 | 1a | 1 | 70 | | |
| 23 | 13 | 26 | 1a | 1 | 73 | 4 | S |

Examples 24 to 41

By using the same method as described in Example 1 and using optically active amine compounds, the chiral Ru complexes shown in Table 2 were synthesized. The complex catalysts and carbonyl compounds were added to a mixture of formic acid and triethylamine (5:2), for reaction at room temperature for a given period. After completion of the reaction, the reaction mixture was diluted with water, to extract the product in ethyl acetate. After drying the organic phase over anhydrous sodium sulfate and evaporating the solvent off, ¹H-NMR (CDCl₃) was analyzed to calculate the conversion. The optical purity and absolute configuration were determined by HPLC or GLC. The results are collectively shown in Table 5. The conversion and optical purity of each sampled reaction solution can be calculated simultaneously by GLC.

In accordance with the present invention, optically active alcohols can be produced at a high optical purity and a high synthetic yield.

TABLE 5

| Examples | Ru complex | Carbonyl compounds | Time | % conv | % ee | config. |
|---|---|---|---|---|---|---|
| 24 | 27(S, S) | 1a | 24 | >99 | 98 | S |
| 25 | 27(S, S) | 1b | 60 | >99 | 97 | S |
| 26 | 27(S, S) | m-1f | 21 | >99 | 97 | S |
| 27 | 27(S, S) | p-1f | 24 | >99 | 95 | S |
| 28 | 27(S, S) | m-1g | 20 | >99 | 98 | S |
| 29 | 27(S, S) | p-1g | 50 | >99 | 97 | S |
| 30 | 27(S, S) | p-1h | 14 | >99 | 90 | S |
| 31 | 27(S, S) | 1i | 60 | >99 | 95 | S |
| 32 | 27(S, S) | 2 | 60 | 93 | 83 | S |
| 33 | 27(S, S) | 3 | 22 | >99 | 96 | S |
| 34 | 27(S, S) | 5 | 60 | >54 | 66 | S |
| 35 | 27(S, S) | 6 | 48 | >99 | 99 | S |
| 36 | 27(S, S) | 7 | 48 | >99 | 99 | S |
| 37 | 27(S, S) | 8 | 60 | 70 | 82 | S |
| 38 | 27(S, S) | 9 | 40 | 47 | 97 | S |
| 39 | 28(R, R) | 10 | 40 | 95 | 99 | R |
| 40 | 28(R, R) | 11 | 65 | 95 | 98 | R |
| 41 | 28(R, R) | 12 | 72 | 68 | 92 | R |

Example B

Production of Optically Active Amines

Production examples of optically active amines are shown below and the present inventive method will be described in detail. Tables 6 and 7 show reaction substrates and asymmetric metal catalysts to be possibly used as typical examples.

The instrumental analysis was done by using the following individual systems.

NMR: JEOL GSX-400/Varian Gemini-200 (¹H-NMR sample: TMS, ³¹P-NMR standard sample: phosphoric acid)

GLC: SHIMADZU GC-17A(column: chiral CP-Cyclodextrin-b-236-M19)

HPLC: JASCO GULLIVER (column: CHIRALCEL OJ, OB-H, OB, OD)

The absolute configurations of the resulting optically active amine compounds were determined on the basis of optical rotation and by HPLC and X-ray structural analysis. Blanks are not definitely shown.

TABLE 6

Imine compounds

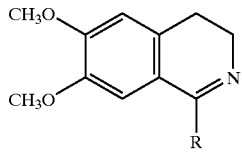
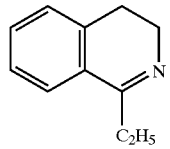

2a: R = CH₃
2b: R = 3,4-(CH₃O)₂C₆H₃CH₂
2c: R = 3,4-(CH₃O)₂C₆H₃(CH₂)₂
2d: R = C₆H₅
2e: R = 3,4-(CH₃O)₂C₆H₅
2f: R = C₆H₅CH₃
2g: R = 1-CH₃C₆H₄

3

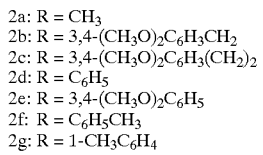

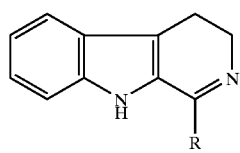

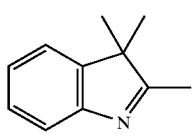

4a: R = CH₃
4b: R = C₆H₅

5

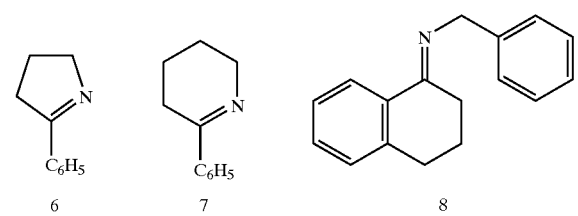

6     7     8

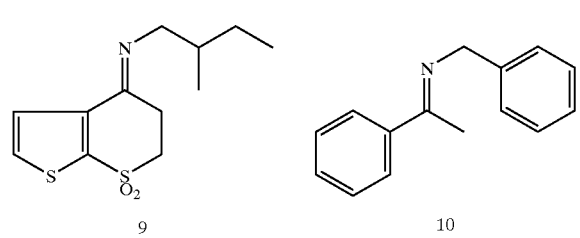

9     10

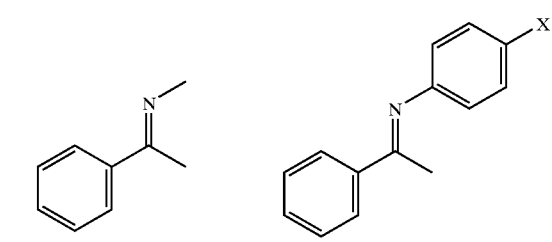

11

12a: X = H
12b: X = Cl
12c: X = CH₃O

TABLE 6-continued

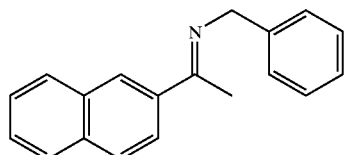

13

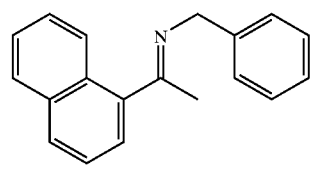

14

Enamine compounds

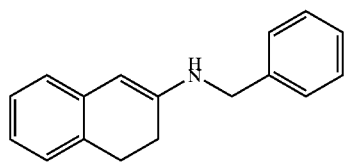

15

TABLE 7

Asymmetric metal complexes

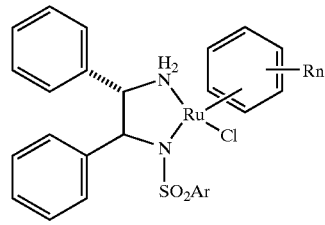

(S,S)-1

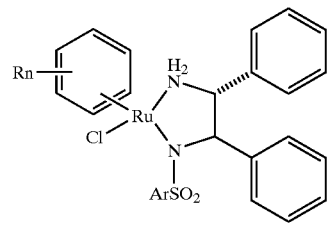

(R,R)-1

TABLE 7-continued a: $\eta^6$-arena - p-cymana; Ar - p-CH$_3$C$_6$H$_4$
b: $\eta^6$-arena - p-cymana; Ar - 2,4,6•(CH$_3$)$_3$C$_6$H$_2$
c: $\eta^6$-arena - benzene; Ar - 1•naphthyl
d: $\eta^6$-arena - benzene; Ar - 2,4,6•(CH$_3$)$_3$C$_6$H$_2$
e: $\eta^6$-arena - benzene; Ar - p-CH$_3$C$_6$H$_4$

Example 42

6,7-Dimethoxy-1-methyl-3,4-dihydroxyisoquinoline (Table 6-2a) (1.03 g, 5 mmol) and a ruthenium catalyst (Table 7) (R, R)-1a (16 mg, 0.025 mmol) were dissolved in acetonitrile (10 ml), followed by addition of a mixture of formic acid-triethylamine (5:2), for agitation at 28° C. for 3 hours. To the reaction mixture was added an aqueous sodium carbonate solution to extract the product in ethyl acetate. After evaporation of the solvent, $^1$H-NMR(CDCl$_3$) of the resulting product was measured to calculate the conversion. Then, the product was purified by silica gel chromatography, to determine the optical purity and absolute configuration of the resulting optically active amine by HPLC or GLC. As collectively shown in Table 8, (S)-6,7-dimethoxy-1-methyl-1,2,3,4-tetrahydroisoquinoline (1.02 g, yield of 99%, 96% ee) was obtained.

Examples 43 to 69

By using the same reactor as in Example 42 but using different reaction substrates, catalysts, reaction solvents and ratios of reaction substrates/catalysts, the same experimental procedures as in Example 42 were carried out. The results are collectively shown in Table 8.

Example 70

Using the same reactor as in Example 42, the enamine compound was used for the same experimental procedures as in Example 42, so that the reaction progressed in a smooth manner, to recover the corresponding optically active amine compound. The results are collectively shown in Table 8.

Comparative Example 1

Under the same conditions as in Example 42, ruthenium-arene catalysts with no optically active amine ligands were used as catalysts, so that the reaction was facilitated, to recover a racemic amine compound quantitatively.

Comparative Example 2

Under the same conditions as in Example 51, ruthenium-arene catalysts with no optically active amine ligands were used as catalysts, so that no reaction was never facilitated.

As has been described above in detail, in accordance with the present invention, optically active amines can be produced at a high yield and an excellent optical purity.

TABLE 8

| Examples | Imines | Catalysts | S/C | Solvents | Time, h | Amines yield % | ee % | absolute configuration |
|---|---|---|---|---|---|---|---|---|
| 42 | 2a | (R,R)-1a | 200 | CH$_3$CN | 3 | 99 | 96 | S |
| 43 | 2a | (R,R)-1a | 200 | CH$_2$Cl$_2$ | 3 | 99 | 94 | S |

TABLE 8-continued

| | | | | | | Amines | | |
|---|---|---|---|---|---|---|---|---|
| Examples | Imines | Catalysts | S/C | Solvents | Time, h | yield % | ee % | absolute configuration |
| 44 | 2a | (S,S)-1a | 200 | $CH_2Cl_2$ | 3 | 99 | 93 | R |
| 45 | 2a | (R,R)-1a | 200 | acetone | 3 | 99 | 95 | S |
| 46 | 2a | (R,R)-1a | 200 | DMF | 3 | 99 | 95 | S |
| 47 | 2a | (R,R)-1a | 200 | DMSO | 3 | 99 | 95 | S |
| 48 | 2a | (R,R)-1a | 1000 | $CH_2Cl_2$ | 98 | 99 | 90 | S |
| 49 | 2b | (S,S)-1a | 200 | $CH_2Cl_2$ | 8 | 81 | 87 | R |
| 50 | 2c | (S,S)-1b | 200 | $CH_2Cl_2$ | 16 | 99 | 92 | R |
| 51 | 2d | (S,S)-1c | 200 | $CH_2Cl_2$ | 8 | 99 | 84 | R |
| 52 | 2e | (S,S)-1c | 100 | $CH_2Cl_2$ | 12 | 96 | 84 | R |
| 53 | 2f | (R,R)-1e | 200 | $CH_2Cl_2$ | 18 | 68 | 82 | |
| 54 | 2g | (R,R)-1e | 200 | $CH_2Cl_2$ | 14 | 94 | 98 | |
| 55 | 3 | (S,S)-1a | 200 | $CH_2Cl_2$ | 16 | 99 | 84 | |
| 56 | 4a | (S,S)-1a | 200 | DMF | 5 | 86 | 97 | R |
| 57 | 4b | (S,S)-1a | 200 | DMF | 5 | 83 | 96 | R |
| 58 | 5 | (R,R)-1e | 200 | $CH_2Cl_2$ | 48 | 59 | 78 | |
| 59 | 6 | (S,S)-1c | 200 | $CH_2Cl_2$ | 39 | 22 | 47 | S |
| 60 | 7 | (S,S)-1c | 200 | $CH_2Cl_2$ | 40 | 100 | 34 | |
| 61 | 8 | (S,S)-1c | 100 | $CH_2Cl_2$ | 6 | 90 | 89 | S |
| 62 | 9 | (S,S)-1c | 100 | $CH_2Cl_2$ | 12 | 64 | 88 | S |
| 63 | 10 | (S,S)-1d | 200 | $CH_2Cl_2$ | 36 | 72 | 77 | S |
| 64 | 11 | (R,R)-1e | 200 | $CH_2Cl_2$ | 15 | 13 | 36 | |
| 65 | 12a | (R,R)-1e | 200 | $CH_2Cl_2$ | 37 | 43 | 46 | |
| 66 | 12b | (R,R)-1e | 200 | $CH_2Cl_2$ | 109 | 35 | 36 | |
| 67 | 12c | (R,R)-1e | 200 | $CH_2Cl_2$ | 65 | 67 | 25 | |
| 68 | 13 | (S,S)-1c | 200 | $CH_2Cl_2$ | 16 | 82 | 64 | |
| 69 | 14 | (S,S)-1e | 200 | $CH_2Cl_2$ | 67 | 71 | 12 | R |
| 70 | 15 | (S,S)-1e | 200 | $CH_2Cl_2$ | 12 | 69 | 43 | |

[In the table, s/c means the molar ratio of substrate/ruthenium-optically active diamine complex.]

Example C
Production of Optically Active Secondary Alcohols by Kinetic Resolution Method of Alcohols Production examples of optically active secondary alcohols are shown below, and the inventive method will further be described in detail. However, the invention is not limited to these examples. Collectively, Table 9 shows racemic secondary alcohols or meso-type diols to be used as typical examples and Table 10 shows ruthenium-diamine complexes.

Abbreviations used in the present Example are as follows. η:representing the number of carbon atoms bonded to the metal of unsaturated ligand; and hexahapto (6 carbon atoms bonded to metal) is expressed as $\eta^6$.

The instrumental analysis was done by using the following individual systems.

NMR: JEOL GSX-400/Varian Gemini-200 ($^1$H-NMR internal standard: TMS)
GLC: SHIMADZU GC-17A(column: chiral CP-cyclodextrin-b-236-M19)
HPLC: JASCO GULLIVER (column: CHIRALCEL OJ, OB-H, OB, OD-H, OD) 81

TABLE 9

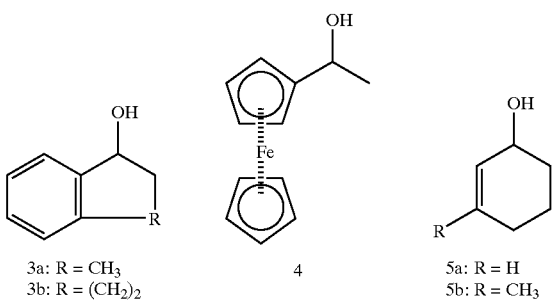

1a: R = H
1b: R = $CH_3O$
1c: R = $(CH_3)_2N$

2a: R = $CH_3$
2b: R = R = $CH_3$

TABLE 9-continued

3a: R = $CH_3$
3b: R = $(CH_2)_2$

4

5a: R = H
5b: R = $CH_3$

6

7

8

9

TABLE 10

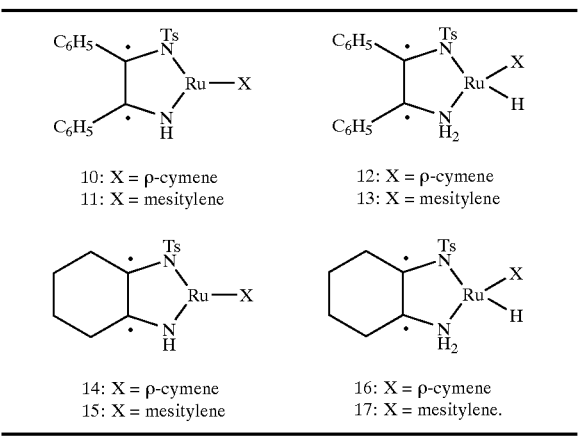

10: X = p-cymene
11: X = mesitylene

12: X = p-cymene
13: X = mesitylene

14: X = p-cymene
15: X = mesitylene

16: X = p-cymene
17: X = mesitylene.

Reference Example 1

Synthesis of RuCl[(S, S)-p-TsNCH($C_6H_5$)CH($C_6H_5$)NH$_2$]($\eta^6$-p-cymene)(chloro((S, S)-N-p-toluenesulfonyl-1,2-diphenylethylenediamine)($\eta^6$-p-cymene)ruthenium

[-RuCl$_2$($\eta^6$-p-cymene)]$_2$(tetrachlorobis ($\eta^6$-p-cymene)diruthenium) (1.53 g; 2.5 mmol) and (S, S)-p-TsNCH($C_6H_5$)CH($C_6H_5$)NH$_2$((S, S)-N-p-toluenesulfonyl-1,2-diphenylethylenediamine) (1.83 g; 5.0 mmol) and triethylamine (1.4 ml; 10 mmol) are dissolved in 2-propanol (50 ml) in a Schlenk's reactor which is preliminarily dried in vacuum and of which the inside is then substituted with argon. The reaction solution was agitated at 80° C. for 1 hour and is then condensed, to recover crystal, which was then filtered and rinsed with a small amount of water, followed by drying under reduced pressure to recover orange crystal (2.99 g). The yield is 94%.

m.p.>100° C. (decomposed)

IR(KBr) [cm$^{-1}$]:3272, 3219, 3142, 3063 3030, 2963, 2874

$^1$H-NMR (400 MHz, $^2$H-chloroform, δ): ppm 1.32 (d, 3H), 1.34 (d, 3H), 2.19 (s, 3H), 2.28 (s, 3H), 3.07 (m, 1H), 3.26 (m, 1H), 3.54 (m, 1H), 3.66 (d, 1H), 5.68 (d, 1H), 5.70 (d, 1H), 5.72 (d, 1H), 5.86 (d, 1H), 6.61 (m, 1H), 6.29–7.20 (m, 14H)

Elemental Analysis
($C_{35}H_{35}ClN_2O_2Rus$)

|  | C | H | N | Cl | Ru |
|---|---|---|---|---|---|
| Theoretical values (%) | 58.53 | 5.54 | 4.40 | 5.57 | 15.89 |
| Elemental values (%) | 58.37 | 5.44 | 4.36 | 5.75 | 18.83 |

The present catalyst was tested by X-ray crystallography. It was indicated that the complex was of a structure satisfying the analysis results.

Reference Example 2

Synthesis of RuCl[(S, S)-p-TsNCH($C_6H_5$)CH($C_6H_5$)NH$_2$]($\eta^6$-Mesitylene)(Chloro((S, S)-N-p-Toluenesulfonyl-1,2-Diphenylethylenediamine) ($\eta^6$-Mesitylene)Ruthenium Instead of [RuCl$_2$($\eta^6$-p-cymene)]$_2$(tetrachlorobis($\eta^6$-p-cymene)diruthenium), [RuCl$_2$($\eta^6$-mesitylene)]$_2$ (tetrachlorobis($\eta^6$-mesitylene)diruthenium) was used, and by the same procedures as in the Reference Example 1, the aforementioned catalyst was recovered as orange crystal. The yield was 64%.

m.p. 218.6–222.5 (decomposed)

$^1$H-NMR (400 MHz, $^2$H-chloroform, δ): ppm 2.24 (3H), 2.38 (s, 9H), 3.69 (dd, 1H), 3.79 (d, 1H), 3.99 (dd, 1H), 4.19 (brd, 1H), 5.30 (s, 3H), 6.65–6.93 (m, 9H), 7.06–7.15 (m, 3H), 7.35 (d, 2H)

Reference Example 3

Synthesis of RuCl[(S, S)-N-p-TS-Cyclohexane-1,2-Diamine]($\eta^6$-p-Cymene)(Chloro-((S, S)-N-p-Toluenesulfonyl-1,2-Cyclohexanediamine)($\eta^6$-p-Cymene)Ruthenium)

Instead of (S, S)-p-TsNCH($C_6H_5$)CH($C_6H_5$)NH$_2$((S, S)-N-p-toluenesulfonyl-1,2-diphenylethylenediamine), (S, S)-N-p-Ts-cyclohexane-1,2-diamine)((S, S)-N-p-toluenesulfonyl-1,2-cyclohexanediamine) was used, and by the same procedures as in the Reference Example 1, the aforementioned catalyst was recovered as orange crystal. The yield is 60%.

Reference Example 4

Synthesis of RuCl[(S, S)-N-p-Ts-Cyclohexane-1,2-Diamine]($\eta^6$-Mesitylene)(Chloro-((S, S)-N-p-Toluenesulfonyl-1,2-Cyclohexanediamine)($\eta^6$-Mesitylene)Ruthenium Instead of (S, S)-p-TsNCH($C_6H_5$)CH($C_6H_5$)NH$_2$((S, S)-N-p-toluenesulfonyl-1,2-diphenylethylenediamine), (s, S)-N-p-Ts-cyclohexane-1,2-diamine)((1S, 2S)-N-p-toluenesulfonyl-1,2-cyclohexanediamine) was used, and by the same procedures as in the Reference Example 2, the aforementioned catalyst was recovered as orange crystal. The yield is 58%.

Example 71-a

Synthesis of Ru[(S, S)-p-TsNCH($C_6H_5$)CH($C_6H_5$)NH]($\eta^6$-p-Cymene)((S, S)-N-p-Toluenesulfonyl-1,2-Diamine)($\eta^6$-p-Cymene)Ruthenium)

[RuCl$_1$($\eta^6$-p-cymene)]$_2$(tetrachlorobis($\eta^6$-p-cymene)diruthenium) (306.2 mg; 0.5 mmol) and (S, S)-p-TsNCH($C_6H_5$)CH($C_6H_5$)NH$_2$((S, S)-N-p-toluenesulfonyl-1,2-diphenylethylenediamine) (366.4 mg; 1.0 mmol) and potassium hydroxide (400 mg; 7.1 mmol) are dissolved in methylenechloride (7 ml) in a Schlenk's reactor which is preliminarily dried in vacuum and of which the inside is then substituted with argon. The reaction solution was agitated at room temperature for 5 minutes, and by adding water (7 ml) to the reaction solution, the color of the reaction solution turned from orange to deep purple. The organic phase was separated and rinsed in water (7 ml). The organic phase was dried over calcium hydroxide, from which the solvent was distilled off. Then, the resulting product was dried under reduced pressure, to recover catalyst No.10 of deep purple crystal (522 mg) in Table 10. The yield is 87%.

m.p.>80° C. (decomposed)

IR(KBr)[cm$^{-1}$]:3289, 3070, 3017, 2968 2920, 2859

$^1$H-NMR (400 MHz, $^2$H-toluene, δ): ppm 1.20 (d, 3H), 1.25 (d, 3H), 2.05 (s, 3H), 2.22 (s, 3H), 2.53 (m, 1H), 4.08 (d, 1H), 4.89 (s, 1H), 5.11 (d, 1H), 5.27 (d, 1H), 5.28 (d, 1H), 5.39 (d, 1H), 5.64 (brd, 1H), 6.87(d, 2H), 7.67 (d, 2H), 7.2–7.7 (m, 10H)

Elemental Analysis
  ($C_{31}H_{34}N_2O_2$RuS)

|  | C | H | N | Ru |
|---|---|---|---|---|
| Theoretical values (%) | 62.09 | 5.71 | 4.67 | 16.85 |
| Elemental values (%) | 62.06 | 5.77 | 4.66 | 16.47 |

The present catalyst was tested by X-ray crystallography. It was indicated that the complex was of a structure satisfying the analysis results.

Example 71-b

Alternative Synthesis of Ru[(S, S)-p-TsNCH($C_6H_5$)CH($C_6H_5$)NH]($\eta^6$-p-Cymene)((S, S)-N-p-Toluenesulfonyl-1,2-Diphenylethylenediamine)($\eta^6$-p-Cymene)Ruthenium)

RuCl[(1S, 2S)-p-TsNCH($C_6H_5$)CH($C_6H_5$)NH$_2$] ($\eta^6$-p-cymene)(chloro-(1S, 2S)-N-p-toluenesulfonyl-1,2-diphenylethylenediamine)($\eta^6$-p-cymene)ruthenium) (318.6 mg; 0.5 mmol) and potassium hydroxide (200 mg; 3.5 mmol) are dissolved in methylene chloride (7 ml) in a Shlenk's reactor which is preliminarily vacuum dried and of which the inside is substituted with argon. The reaction solution was agitated at room temperature for 5 minutes, and by adding water (7 ml) to the reaction solution, the color of the reaction solution turned from orange to deep purple. The organic phase was separated and rinsed in water (7 ml). The organic phase was dried over calcium hydroxide, from which the solvent was distilled off. Then, the resulting product was dried under reduced pressure, to recover crystal in deep purple crystal (522 mg). The yield is 87%.

Example 72-a

Synthesis of Ru[(S, S)-p-TsNCH($C_6H_5$)CH($C_6H_5$)NH]($\eta^6$-Mesitylene)(((S, S)-N-p-Toluenesulfonyl-1, 2-Diphenylethylenediamine) ($\eta^6$-Mesitylene) Ruthenium)

Instead of (RuCl$_2$($\eta^6$-p-cymene)]$_2$(tetrachlorobis($\eta^6$-p-cymene)diruthenium), [RuCl$_2$($\eta^6$-mesitylene)]$_2$ (tetrachlorobis($\eta^6$-mesitylene)diruthenium) was used, and by the same procedures as in the Example 71-a, the catalyst in purple crystal as No.11 in Table 10 was recovered. The yield is 80%.

$^1$H-NMR (400 MHz, $^2$H-chloroform, δ) ppm 1.91 (s. 9H). 1.99 (s. 3H). 3.83 (d. 1H). 4.51 (s. 1H). 4.95 (s. 3H). 5.92 (brd. 1H). 6.38–7.71 (m. 14H)

Example 72-b

Alternative Synthesis of Ru((S, S)-p-TsNCH($C_6H_5$)CH($C_6H_5$)NH]($\eta^6$-Mesitylene)(((S, S)-N-p-Toluenesulfonyl-1,2-Diphenylethylenediamine)($\eta^6$-Mesitylene)Ruthenium)

Instead of RuCl[(S, S)-p-TsNCH($C_6H_5$)CH($C_6H_5$)NH$_2$]($\eta^6$-p-cymene)(chloro-((S, S)-N-p-toluenesulfonyl-1,2-diphenylethylenediamine)($\eta^6$-p-cymene)ruthenium), RuCl[(S, S)-p-TsNCH($C_6H_5$)CH($C_6H_5$)NH$_2$]($\eta^6$-mesitylene)(chloro-((S, S)-N-p-toluenesulfonyl-1,2-diphenylethylenediamine) ($\eta^6$-mesitylene)ruthenium) synthesized as in the Reference Example 2 was used, and by the same procedures as in the Example 71-b, the catalyst in purple crystal was recovered. The yield is 90%.

Example 73-a

Synthesis of Ru[(S, S)-N-p-Ts-1,2-Cyclohexanediamine]($\eta^6$-p-Cymene)(((S, S)-N-p-Toluenesulfonyl-1,2-Cyclohexanediamine) ($\eta^6$-p-Cymene)Ruthenium)

Instead of (S, S)-p-TsNCH($C_6H_5$)CH($C_6H_5$)NH$_2$]((S, S)-N-p-toluenesulfonyl-1,2-diphenylethylenediamine), (S, S)-N-p-Ts-1,2-cyclohexanediamine((1S, 2S)-N-p-toluenesulfonyl-1,2-cyclohexanediamine) was used, and by the same procedures as in the Example 71-a, the catalyst in purple crystal as No.14 in Table 10 was recovered. The yield is 58%.

Example 73-b

Alternative Synthesis of Ru[(S, S)-N-p-Ts-1,2-Cyclohexanediamine]($\eta^6$-p-Cymene) (((S, S)-N-p-Toluenesulfonyl-1,2-Cyclohexanediamine)($\eta^6$-p-Cymene)Ruthenium)

Instead of RuCl[(S, S)-p-TsNCH($C_6H_5$)CH($C_6H_5$)NH$_2$]) ($\eta^6$-p-cymene)(chloro-((S, S)-N-p-toluenesulfonyl-1,2-diphenylethylenediamine)($\eta^6$-p-cymene)ruthenium), RuCl[(S, S)-N-p-Ts-cyclohexane-1,2-diamine synthesized in the Reference Example 3 was used, and by the same procedures as in the Example 71-b, the catalyst in purple crystal was recovered. The yield is 62%.

Example 74-a

Synthesis of Ru[(S, S)-N-p-TS-1,2-Cyclohexanediamine]($\eta^6$-Mesitylene)((S, S)-N-p-Toluenesulfonyl-1,2-Cyclohexanediamine)($\eta^6$-Mesitylene)Ruthenium)

Instead of (S, S)-p-TsNCH($C_6H_5$)CH($C^6H_5$)NH$_2$((S, S)-N-p-toluenesulfonyl-1,2-diphenylethylenediamine), (S, S)-N-p-Ts-cyclohexane-1,2-diamine ((S, S)-N-p-toluenesulfonyl-1,2-cyclohexanediamine) was used, and by the same procedures as in the Example 71-a, the catalyst as No.15 shown in Table 10 was recovered as purple crystal. The yield is 60%.

Example 74-b

Alternative Synthesis of Ru[(S, S)-N-p-Ts-1,2-Cyclohexanediamine]($\eta^6$-Mesitylene) ((S, S)-N-p-Toluenesulfonyl-1,2-Cyclohexanediamine)($\eta^6$-Mesitylene)Ruthenium)

Instead of RuCl[(S, S)-p-TsNCH($C_6H_5$)CH($C_6H_5$)NH$_2$]($\eta^6$-p-cymene)(chloro-(S, S)-N-p-toluenesulfonyl-1,2-diphenylethylenediamine)($\eta^6$-p-cymene)ruthenium), RuCl[(S, S)-N-p-TS-1,2-cyclohexanediamine]($\eta^6$-mesitylene) (chloro-(1S, 2S)-N-p-toluenesulfonyl-1,2-cyclohexanediamine)($\eta^6$-mesitylene)ruthenium) synthesized in the Reference Example 4 was used, and by the same procedures as in the Example 71-b, the aforementioned catalyst was recovered as purple crystal. The yield is 62%.

Example 75-a

Synthesis of RuH[(S, S)-p-TsNCH($C_6H_5$)CH($C_6H_5$)NH$_2$]($\eta^6$-p-Cymene)(Hydride-(S, S)-N-p-Toluenesulfonyl-1,2-Diphenylethylenediamine)($\eta^6$-p-Cymene)Ruthenium)

Ru[(S, S)-p-TsNCH($C_6H_5$)CH($C_6H_5$)NH]($\eta^6$-p-cymene) ((S, S)-N-p-toluenesulfonyl-1,2-diphenylethylenediamine) ($\eta^6$-p-cymene)ruthenium) (600 mg; 1.0 mmol) is dissolved in 2-propanol (10 ml) in a Shlenk's reactor which is preliminarily vacuum dried and of which the inside is substituted with argon. The reaction solution was agitated at room temperature for 15 minutes. The solvent was recovered under reduced pressure at room temperature, to recover a compound in brown yellow. After rinsing the compound in cool pentane and recrystallizing the compound in methanol, the catalyst No.12 in Table 10 was recovered as orange crystal. The yield is 85%.

m.p. >60° C. (decomposed)

IR(KBr)[cm$^{-1}$]:3335, 3317, 3228, 3153, 3060, 3025, 2960, 2917, 2867

$^1$H-NMR (400 MHz, $^2$H-chloroform, δ):ppm −5.47 (s, 1H), 1.53 (d, 3H), 1.59 (d, 3H), 2.29 (d, 3H), 2.45 (s, 3H), 2.79 (m, 1H), 2.93 (m, 1H), 3.80 (d, 1H), 4.02 (m, 1H), 5.15 (d, 1H), 5.19 (d, 1H), 5.29 (m, 1H), 5.43 (d, 1H), 5.58 (d, 1H), 6.49 (d, 2H), 6.9–7.3 (m, 10H), 7.59 (d, 2H)

Elemental Analysis ($C_{31}H_{36}N_2O_2RuS$)

|  | C | H | N | Ru |
|---|---|---|---|---|
| Theoretical values (%) | 61.88 | 6.02 | 4.66 | 16.80 |
| Experimental values (%) | 61.79 | 5.94 | 4.70 | 16.56 |

The X-ray crystallography shows that the complex was of a structure satisfying the analytical results.

Example 75-b

Alternative synthesis of RuH[(S, S)-p-TsNCH($C_6H_5$)CH($C_4H_5$)NH$_2$(η$^6$-p-Cymene) (Hydride-((S, S)-N-p-Toluenesulfonyl-1,2-Diphenylethylenediamine) (η$^6$-p-Cymene) Ruthenium)

Toluene (7 ml) was added into the Ru[(S, S)-p-TsNCH($C_6H_5$)CH($C_6H_5$)NH](η$^6$-p-cymene)((S, S)-N-p-toluenesulfonyl-1,2-diphenylethylenediamine)(η$^6$-p-cymene)ruthenium) (306.2 mg; 0.5 mmol) synthesized in the Example 72 in an autoclave which was preliminarily vacuum dried and of which the inside was substituted with argon, for reaction at room temperature and a hydrogen pressure of 80 atm. After elimination of the solvent and rinsing in cool pentane and subsequent recrystallization in methanol, crystal in orange (420 mg) was recovered. The yield is 70%.

Example 76-a

Synthesis of RuH (S, S)-p-TsNCH($C_6H_5$)CH($C_6H_5$)NH$_2$](η$^6$-Mesitylene) (Hydride-((S, S)-N-p-Toluenesulfonyl-1,2-Diphenylethylenediamine) (η$^6$-Mesitylene)Ruthenium)

Instead of Ru[(S, S)-p-TsNCH($C_6H_5$)CH($C_6H_5$)NH$_2$](η$^6$-p-cymene)(((S, S)-N-p-toluenesulfonyl-1,2-diphenylethylenediamine) (η$^6$-p-cymene)ruthenium), Ru[(S, S)-p-TsNCH($C_6H_5$)CH($C_6H_5$)NH](η$^6$-mesitylene) (((S, S)-N-p-toluenesulfonyl-1,2-diphenylethylenediamine) (η$^6$-mesitylene)ruthenium) synthesized in the Example 72 was used, and by the same procedures as in the Example 75-a, the aforementioned catalyst No.13 in Table 10 was recovered. The yield was 60%.

Example 76-b

Alternative Synthesis of RuH[(S, S)-p-TsNCH($C_6H_5$)CH($C_6H_5$)NH$_2$](η$^6$-Mesitylene)(Hydride-((S, S)-N-p-Toluenesulfonyl-1,2-Diphenylethylenediamine)(η$^6$-Mesitylene) Ruthenium)

Instead of Ru((S, S)-p-TsNCH($C_6H_5$)CH($C_6H_5$)NH](η$^6$-p-cymene)(((S, S)-N-p-toluenesulfonyl-1,2-diphenylethylenediamine) (η$^6$-p-cymene)ruthenium), Ru[(S, S)-p-TsNCH($C_6H_5$)CH($C_6H_5$)NH](η$^6$-mesitylene) (((S, S)-N-p-toluenesulfonyl-1,2-diphenylethylenediamine) (η$^6$-mesitylene)ruthenium) synthesized in the Example 72 was used, and by the same procedures as in the Example 75-b, the aforementioned catalyst was recovered. The yield is 60%.

Example 77-a

Synthesis of RuH[(S, S)-N-p-Ts-1,2-Cyclohexanediamine](η$^6$-p-Cymene)(Hydride-(S, S)-N-p-Toluenesulfonyl-1,2-Cyclohexanediamine) (η$^6$-p-Cymene)Ruthenium)

Instead of Ru[(S, S)-p-TsNCH($C_6H_5$)CH($C_6H_5$)NH](η$^6$-p-cymene)((S, S)-N-p-toluenesulfonyl-1,2-diphenylethylenediamine) (η$^6$-p-cymene)ruthenium), Ru[(S, S)-N-p-Ts-1,2-cyclohexanediamine](η$^6$-p-cymene) ((S, S)-N-p-toluenesulfonyl-1,2-cyclohexanediamine)(η$^6$-p-cymene)ruthenium) synthesized in the Example 73 was used, and by the same procedures as in the Example 75-a, the catalyst No.16 in Table 10 was recovered. The yield is 54%.

Example 77-b

Alternative Synthesis of RUH[(S, S)-N-p-Ts-1,2-Cyclohexanediamine](η$^6$-p-Cymene)(Hydride-(S, S)-N-p-Toluenesulfonyl-1,2-Cyclohexanediamine) (η$^6$-p-Cymene)Ruthenium)

Instead of Ru[(S, S)-p-TsNCH($C_6H_5$)CH($C_6H_5$)NH](η$^6$-p-cymene)(chloro-(S, S)-N-p-toluenesulfonyl-1,2-diphenylethylenediamine) (η$^6$-p-cymene)ruthenium), Ru[(S, S)-N-p-Ts-1,2-cyclohexanediamine](η$^6$-p-cymene) ((S, S)-N-p-toluenesulfonyl-1,2-cyclohexanediamine)(η$^6$-p-cymene)ruthenium) synthesized in the Example 73 was used, and by the same procedures as in the Example 75-b, the catalyst was recovered. The yield is 55%.

Example 78-a

Synthesis of RuH[(S, S)-N-p-Ts-1,2-Cyclohexanediamine](η$^6$-Mesitylene)(Hydride(S, S)-N-p-Toluenesulfonyl-1,2-Cyclohexanediamine) (η$^6$-Mesitylene)Ruthenium)

Instead of Ru[(S, S)-p-TsNcH($C_6H_5$)CH($C_6H_5$)NH](η$^6$-p-cymene)((S, S)-N-p-toluenesulfonyl-1,2-diphenylethylenediamine)(η$^{60}$-p-cymene)ruthenium), Ru[(S, S)-N-p-Ts-1,2-cyclohexanediamine](η$^6$-mesitylene) ((S, S)-N-p-toluenesulfonyl-1,2-cyclohexanediamine)(η$^6$-mesitylene)ruthenium) synthesized in the Example 74 was used, and by the same procedures as in the Example 75-a, the catalyst No.17 in Table 10 was recovered. The yield is 52%.

Example 78-b

Alternative Synthesis of RuH[(S, S)-N-p-Ts-1,2-Cyclohexanediamine](η$^6$-Mesitylene)(Hydride((S, S)-N-p-Toluenesulfonyl-1,2-Cyclohexanediamine) (η$^6$-Mesitylene)Ruthenium)

Instead of Ru[(S, S)-p-TsNCH($C_6H_5$)CH($C_6H_5$)NH](η$^6$-p-cymene)((S, S)-N-p-toluenesulfonyl-1,2-diphenylethylenediamine) (η$^6$-p-cymene)ruthenium), Ru[(S, S)-N-p-Ts-1,2-cyclohexanediamine](η$^6$-mesitylene) ((S, S)-N-p-toluenesulfonyl-1,2-cyclohexanediamine)(η$^6$-mesitylene)ruthenium) synthesized in the Example 74 was used, and by the same procedures as in the Example 75-b, the aforementioned catalyst was recovered. The yield is 48%.

Example 79

Synthesis of (R)-1-Indanol

Ru[(S, S)-p-TsNCH($C_6H_5$)CH($C_6H_5$)NH]($\eta^6$-p-cymene) ((S, S)-N-p-toluenesulfonyl-1,2-diphenylethylenediamine) (ruthenium-$\eta^6$-p-cymene mesitylene (6.0 mg; 10 μmmol) synthesized in the Example 71 and 1-indanol (671 mg; 5 mmol) were weighed in a Shlenk's reactor which was preliminarily vacuum dried and of which the inside was substituted with argon, and acetone (2.5 ml) was then added to the resulting mixture for agitation at 28° C. for 6 hours. The solvent was distilled off under reduced pressure, prior to separation by silica gel chromatography (eluent; ethyl acetate:hexane=1:3), to recover (R)-indanol (286 mg) in colorless crystal. The yield is 84%.

m.p. 71–72° C.

$[\alpha]^{24}_D = -30.1°$ (c=1.96, chloroform)

The resulting (R)-1-indanol was analyzed by HPLC (high-performance liquid chromatography), and the objective (R)-1-indanol was at an optical purity of 97% ee.

<HPLC Analytical Conditions>

Column: Chiralcel OB (manufactured by Daicell Chemical Industry, Co.)

Developing solution: isopropanol: hexane=10:90

Flow rate: 0.5 ml/min

Retention time: (S)-1-indanol 18.6 minutes (R)-1-indanol 12.9 minutes.

Examples 80 to 93

According to the method described in Example 79, the optically active ruthenium-diamine complexes for racemic secondary alcohols and meso-type diols as reaction substrates as shown in Table 9 were used for reaction under reaction conditions of reaction time, to recover the individually corresponding optically active secondary alcohols at high yields. The results are collectively shown in Table 11.

TABLE 11

| Examples | Sub-strates | Catalysts | s/c | Reaction time (hr) | % (yield) | % ee | Products |
|---|---|---|---|---|---|---|---|
| 80 | 1a | (S,S)-10 | 500 | 36 | 50 | 92 | 1a(R) |
| 81 | 1a | (S,S)-11 | 500 | 30 | 51 | 94 | 1a(R) |
| 82 | 1a | (S,S)-10 | 500 | 22 | 47 | 92 | 1b(R) |
| 83 | 1b | (S,S)-11 | 500 | 30 | 44 | 98 | 1c(R) |
| 84 | 1c | (S,S)-11 | 500 | 36 | 47 | 97 | 2a(R) |
| 85 | 2a | (S,S)-11 | 500 | 24 | 47 | 97 | 2b(R) |
| 79 | 2b | (S,S)-10 | 500 | 6 | 46 | 97 | 3a(R) |
| 86 | 3a | (S,S)-10 | 500 | 6 | 49 | 99 | 3b(R) |
| 87 | 3b | (S,S)-11 | 500 | 36 | 51 | 98 | 4(R) |
| 88 | 4 | (S,S)-10 | 500 | 4.5 | 43 | 93 | 5a(R) |
| 89 | 5a | (S,S)-10 | 500 | 5 | 46 | 95 | 5b(R) |
| 90 | 5b | (S,S)-11 | 200 | 3 | 70 | 96 | 7 |
| 91 | 5 | (S,S)-10 | 200 | 3 | 56 | 87 | 9 |
| 92 | 1a | (S,S)-14 | 500 | 36 | 48 | 82 | 1a(R) |
| 93 | 1a | (S,S)-15 | 500 | 36 | 48 | 86 | 1a(R) |

(In the table, s/c means the molar ratio of substrate/ruthenium-optically active diamine complex.)

INDUSTRIAL APPLICABILITY

In accordance with the present invention, optically active alcohols and optically active amines are provided, which are useful in various fields of pharmaceutical products, synthetic intermediates thereof, food, flavor, cosmetics, liquid crystal materials and the like.

The ruthenium-diamine complex of the present invention is industrially useful as a chiral catalyst providing higher selectivity and activity in that the complex can be used for organic synthesis such as asymmetric synthetic reactions. If the complex is used as a hydrogen transfer-type asymmetric reduction catalyst of racemic secondary alcohols or meso-type diols, optically active secondary alcohols useful as production intermediates of drugs can be produced highly efficiently.

What is claimed is:

1. An optically active catalyst composed of a transition metal catalyst and an optically active amine derivative represented by any one of the following formulas:

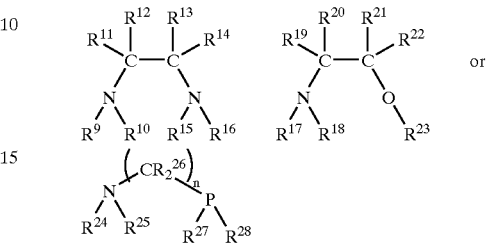

wherein $R^9$, $R^{10}$, $R^{15}$ and $R^{16}$ are independently hydrogen, a saturated or unsaturated hydrocarbon group, urethane group or sulfonyl group; $R^{11}$, $R^{12}$, $R^{13}$ and $R^{14}$ are the same or different so that the carbon bonded with these substituent groups might occupy the asymmetric center and independently represent hydrogen atom, an aromatic group, a saturated or unsaturated hydrocarbon group or cyclic hydrocarbon group; any one of $R^{11}$ and $R^{12}$ and any one of $R^{13}$ and $R^{14}$ are bonded together to form a ring;

at least one of $R^{17}$ and $R^{18}$ is hydrogen atom, and the remaining one is hydrogen atom, a saturated or unsaturated hydrocarbon group, urethane group or sulfonyl group; $R^{19}$, $R^{20}$, $R^{21}$ and $R^{22}$ are the same or different so that the carbon bonded with these substituent groups might occupy the asymmetric enter and independently represent hydrogen atom, an aromatic group, a saturated or unsaturated hydrocarbon group or cyclic hydrocarbon group; $R^{23}$ represents hydrogen atom, an aromatic group, a saturated or unsaturated hydrocarbon group or cyclic hydrocarbon group; furthermore, any one of $R^{19}$ and $R^{20}$ and any one of $R^{21}$ and $R^{22}$ may be bonded together to form a ring or any one of $R^{17}$ and $R^{18}$ and any one of $R^{20}$ and $R^{21}$ may be bonded together to form a ring;

$R^{24}$ and $R^{25}$ are independently hydrogen atom, a saturated or unsaturated hydrocarbon group, urethane group, sulfonyl group or acyl group; $(CR_2^{26})_n$ are the same or different so that the carbon bonded with these substituent groups might occupy the asymmetric center; $R^{26}$ represents hydrogen atom, an aromatic group, a saturated or unsaturated hydrocarbon group or cyclic hydrocarbon group; $R^{27}$ and $R^{28}$ independently represent hydrogen atom, and or a saturated or unsaturated hydrocarbon group.

2. A catalyst according to claim 1, wherein the transition metal catalyst is a complex of metals of group VIII as represented by the following general formula:

MXmLn wherein M represents transition metals of group VII selected from the group consisting of iron, cobalt, nickel, ruthenium, rhodium, iridium, osmium, palladium and platinum; X represents hydrogen, halogen atom, carboxyl group, hydroxy group and or alkoxy group;

L represents neutral ligands selected from the group consisting of aromatic compounds and olefin compounds; and m and n represent an) integer.

3. An optically active catalyst composed of a transition metal catalyst and an optically active amine derivative represented by any one of the following formulas:

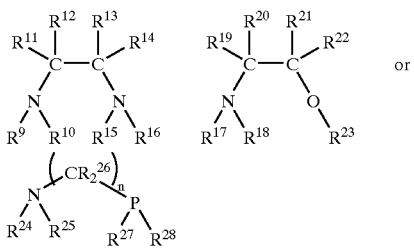

wherein $R^9$, $R^{10}$, $R^{15}$ and $R^{16}$ are independently hydrogen, a saturated or unsaturated hydrocarbon group, urethane group or sulfonyl group; $R^{11}$, $R^{12}$, $R^{13}$ and $R^{14}$ are the same or different so that the carbon bonded with these substituent groups might occupy the asymmetric center and independently represent hydrogen atom, an aromatic group, a saturated or unsaturated hydrocarbon group or cyclic hydrocarbon group; any one of $R^{11}$ and $R^{12}$ and any one of $R^{13}$ and $R^{14}$ are bonded together to form a ring;

at least one of $R^{17}$ and $R^{18}$ is hydrogen atom, and the remaining one is hydrogen atom, a saturated or unsaturated hydrocarbon group, urethane group or sulfonyl group; $R^{19}$, $R^{20}$, $R^{21}$ and $R^{22}$ are the same or different so that the carbon bonded with these substituent groups might occupy the asymmetric center and independently represent hydrogen atom, an aromatic group, a saturated or unsaturated hydrocarbon group or cyclic hydrocarbon group; $R^{23}$ represents hydrogen atom, an aromatic group, a saturated or unsaturated hydrocarbon group or cyclic hydrocarbon group; furthermore, any one of $R^{19}$ and $R^{20}$ and any one of $R^{21}$ and $R^{22}$ may be bonded together to form a ring or any one of $R^{17}$ and $R^{18}$ and any one of $R^{20}$ and $R^{21}$ may be bonded together to form a ring;

$R^{24}$ and $R^{25}$ are independently hydrogen atom, a saturated or unsaturated hydrocarbon group, urethane group, sulfonyl group or acyl group; $(CR_2^{26})_n$ are the same or different so that the carbon bonded with these substituent groups might occupy the asymmetric center; $R^{26}$ represents hydrogen atom, an aromatic group, a saturated or unsaturated hydrocarbon group or cyclic hydrocarbon group; furthermore, $R^{27}$ and $R^{28}$ independently represent hydrogen atom, or a saturated or unsaturated hydrocarbon group.

4. A catalyst according to claim 3, wherein the transition metal catalyst is a complex of metals of group VIII.

5. An optically active catalyst according to claim 4, wherein the transition metal catalyst is an optically active ruthenium-diamine complex represented by the following general formula (VII):

(VII)

wherein * represents an asymmetric carbon atom; $R^{01}$ and $R^{02}$ are the same or different, independently representing alkyl group, or phenyl group or cycloalkyl group which may or may not be substituted with an alkyl group; or $R^{01}$ and $R^{02}$ together form an alicyclic ring unsubstituted or substituted with an alkyl group; $R^{03}$ represents methanesulfonyl group, trifluoromethanesulfonyl group, naphthylsulfonyl group, camphor sulfonyl group, or benzenesulfonyl group which may or may not be substituted with an alkyl group, an alkoxyl group or halogen atom, or benzoyl group which may or may not be substituted with alkoxycarbonyl group or alkyl group; $R^{04}$ represents hydrogen atom or alkyl group; X represents an aromatic compound which may or may not be substituted with an alkyl group; and m and n together represent 0 or 1.

6. An optically active ruthenium-diamine complex, represented by the following general formula VII:

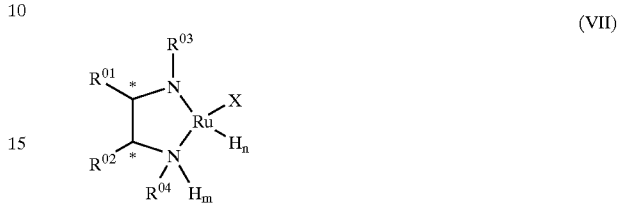

(VII)

wherein * represents an asymmetric carbon atom; $R^{01}$ and $R^{02}$ are the same or different, independently representing alkyl group, or phenyl group or cycloalkyl group which may or may not be substituted with an alkyl group; or $R^{01}$ and $R^{02}$ together form an alicyclic ring unsubstituted or substituted with an alkyl group; $R^{03}$ represents methanesulfonyl group, trifluoromethanesulfonyl group, naphthylsulfonyl group, camphor sulfonyl group, or benzenesulfonyl group which may or may not be substituted with an alkyl group, an alkoxyl group or halogen atom, or benzoyl group which may or may not be substituted with alkoxycarbonyl group or alkyl group; $R^{04}$ represents hydrogen atom or alkyl group; X represents an aromatic compound which may or may not be substituted with an alkyl group; and m and n together represent 0 or 1.

7. An optically active ruthenium-diamine complex according to claim 6, wherein $R^{01}$ and $R^{02}$ are independently phenyl group or together form an alicyclic ring, unsubstituted or substituted with an alkyl group.

8. A method for producing optically active secondary alcohols, comprising subjecting racemic secondary alcohols or meso-type diols to hydrogen transfer reaction in the presence of an optically active ruthenium-diamine complex catalyst according to claim 5.

9. A method according to claim 8, comprising the reaction of racemic secondary alcohols or mesa-type diols represented by the following formulas (VIII) and (IX):

(VIII)

(IX)

wherein $R^6$ an aromatic monocyclic or polycyclic hydrocarbon group, unsubstituted or substituted or a hetero monocyclic or polycyclic group containing hetero atoms, or ferrocenyl group; $R^7$ represents hydrogen atom, a saturated or unsaturated hydrocarbon group, or a functional group containing hetero atoms; or $R^6$ and $R^7$ may be bonded together to form a saturated or unsaturated alicyclic group having a cyclic ketone and the alicyclic group may or may not be substituted;

$R^8$ and $R^9$ furthermore independently represent a saturated or unsaturated hydrocarbon group which may or may not have a substituent, or $R^7$ and $R^9$ may be bonded together to form a saturated or unsaturated alicyclic group which may or may not have a substituent; and n is 1 or 2.

* * * * *